United States Patent [19]

Press et al.

[11] Patent Number: 5,284,857
[45] Date of Patent: * Feb. 8, 1994

[54] SUBSTITUTED THIENOPYRANS AS ANTIHYPERTENSIVE AGENTS

[75] Inventors: Jeffery B. Press, Penllyn, Pa.; Pauline Sanfilippo, Flemington, N.J.; James J. McNally, High Bridge, N.J.; Robert Falotico, Belle Mead, N.J.

[73] Assignee: Ortho Pharmaceutical Corporation, Raritan, N.J.

[*] Notice: The portion of the term of this patent subsequent to Feb. 12, 2008 has been disclaimed.

[21] Appl. No.: 631,593

[22] Filed: Dec. 21, 1990

Related U.S. Application Data

[63] Continuation-in-part of Ser. No. 401,628, Sep. 6, 1989, abandoned, which is a continuation-in-part of Ser. No. 249,043, Sep. 23, 1988, Pat. No. 4,992,435.

[51] Int. Cl.⁵ .................... A61K 31/38; C07D 497/04
[52] U.S. Cl. .................... 514/321; 514/210; 514/212; 514/422; 514/443; 540/362; 540/454; 540/524; 540/596; 546/197; 548/454; 548/526; 548/965; 549/50
[58] Field of Search ............... 540/362, 454, 524, 596; 546/197; 548/454, 526, 962; 549/50; 514/212, 210, 321, 422, 443

[56] References Cited

U.S. PATENT DOCUMENTS

| | | | |
|---|---|---|---|
| 4,797,413 | 1/1989 | Baldwin et al. | 546/197 |
| 4,824,968 | 4/1989 | Ponticello et al. | 546/197 |
| 4,992,465 | 2/1991 | Hutchinson | 540/596 |
| 5,030,736 | 6/1991 | Press et al. | 549/50 |
| 5,077,307 | 12/1991 | Binder et al. | 546/197 |
| 5,095,032 | 3/1992 | Bertram et al. | 549/50 |
| 5,120,757 | 6/1992 | Baldwin et al. | 546/197 |

Primary Examiner—James H. Reamer
Assistant Examiner—John Peabody
Attorney, Agent, or Firm—John Harbour

[57] ABSTRACT

Substituted thienopyrans and processes for preparing the thienopyrans are disclosed. The thienopyrans are useful as antihypertensive agents; antianginals are peripheral antivasoconstrictive agents.

8 Claims, No Drawings

SUBSTITUTED THIENOPYRANS AS ANTIHYPERTENSIVE AGENTS

This is a continuation-in-part of application Ser. No. 401,628, filed Sept. 6, 1989, now abandoned which in turn is a continuation-in-part of application Ser. No. 249,043, filed Sept. 23, 1988 now U.S. Pat. No. 4,992,435.

FIELD OF THE INVENTION

The present invention relates to substituted thienopyran derivatives of the formula:

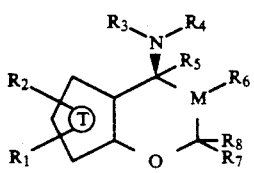

wherein

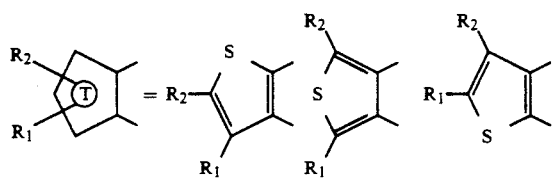

and $R_1$ and $R_2$ are selected from the group consisting of hydrogen, nitro, cyano, trifluoromethyl, halogen such as bromo, chloro, iodo, alkyl ($C_{1-4}$), acyl ($C_{2-4}$), substituted acyl ($C_{2-4}$) (wherein the substituent is halogen such as bromo, chloro, fluoro or iodo), benzoyl, substituted benzoyl (wherein the substituent is halogen such as bromo, chloro, iodo, alkyl ($C_{1-4}$), alkoxy ($C_{1-4}$), acyl ($C_{2-4}$), nitro, cyano or trifluoromethyl), alkoxy($C_{1-4}$)carbonyl, CHO, COOH, $CONH_2$, $CON(R)_2$ wherein R is alkyl ($C_{1-4}$), NHCOR wherein R is alkyl ($C_{1-4}$) alkoxy ($C_{1-4}$), phenyl or substituted phenyl [wherein the substituent is halogen such as bromo, chloro, Iodo , lower alkyl ($C_{1-4}$), lower alkoxy ($C_{1-4}$), nitro, cyano, trifluoromethyl or lower acyl ($C_{1-4}$)];

$R_3$ and $R_4$ are selected from the group consisting of hydrogen, hydroxy, acyl ($C_{2-5}$), substituted acyl wherein the substituent is CN or $CF_3$ lower alkyl ($C_{1-4}$), cycloalkyl ($C_{3-6}$), cycloalkyl carbonyl ($C_{3-6}$), pyridyl carbonyl, benzoyl, substituted benzoyl (wherein the substituent is halogen such as bromo, chloro, iodo, lower alkyl ($C_{1-4}$), lower alkoxy ($C_{1-4}$), lower acyl ($C_{2-4}$), trifluoromethyl, nitro, cyano RCONH wherein R is alkyl ($C_{1-4}$)] or $R_3R_4N$ together may form a heterocyclic ring such as a pyrrole, pyrrolidine or piperidine ring or a lactam having 3-9 carbon atoms and containing one or more heteroatoms such as a pyridinone, pyrazinone, pyrrolidinone, glycine anhydride, isoindolone or piperidinone or a substituted lactam having 3-9 carbon atoms [wherein the substituent is hydroxy, lower alkoxy ($C_{1-4}$), lower acyl ($C_{2-4}$), halogen such as bromo, chloro, iodo, lower alkyl ($C_{1-4}$), nitro, cyano or trifluoromethyl];

$R_5$ is hydrogen or together with $R_6$ forms a double bond;

m is carbonyl, or CH or nitrogen when $R_5$ and $R_6$ form a double bond;

when M is CH, $R_6$ is hydroxy, alkoxy ($C_{1-6}$), acyloxy ($C_{2-7}$ ), benzoyloxy, or substituted benzoyloxy (wherein the substituent is halogen such as bromo, chloro, iodo, lower alkyl ($C_{1-4}$), lower alkoxy ($C_{1-4}$), lower acyl ($C_{2-4}$), nitro, cyano or trifluoromethyl); and $R_7$ and $R_8$ are hydrogen or alkyl ($C_{1-4}$) and together may form a ring having 5-8 carbon atoms; and optical isomers thereof.

The preferred compounds of the present invention are those wherein m is CH. The substituted thienopyran derivatives are relaxants of smooth muscle tone and as such have utility in vascular tissue for the treatment of hypertensive disease, angina, cardioprotection and other vascular disorders characterized by poor regional perfusion (e.g. Raynaud's disease). Other possible utilities include bronchodilation, uterine relaxation, gut motility disorders, alopecia, asthma and treatment of incontinence and glaucoma. These compounds also are intermediates in the preparation of agents having similar pharmacological properties.

DESCRIPTION OF THE PRIOR ART

European Patent Application No. 120 426 describes substituted benzopyrans useful as antihypertensive agents having the following formula:

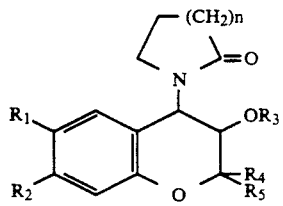

European Patent Application No. 139992 describes substituted benzopyrans useful as antihypertensive agents having the following formula:

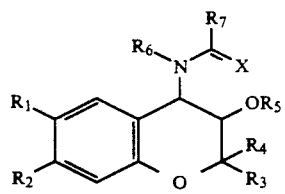

European Patent Application No. 205 292 describes substituted pyrano [3,2-c] pyridine derivatives useful as antihypertensive agents having the following formula:

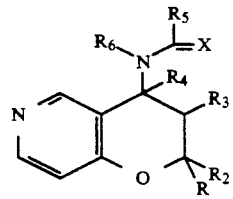

British Patent No. 013786 describes pyrano [3,2-c] pyridine derivatives useful as antihypertensive agents having the following formula:

Thiophene analogs of antiviral flavans having the following formula:

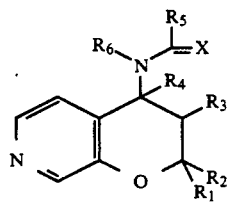

are known in the art [Arch. Pharm. (Weinheim) 318, 70 (1985)].

Thiophene isosteres of flavones and xanthones having the following formula:

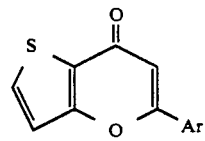

are also known in the art [Tetrahedron, 33, 191 (1977)).

Benzoxazines are disclosed in EP-A 0371312 (E. Merck).

Benzopyran ketones are disclosed in EP-A 0366273 (Beecham).

DETAILED DESCRIPTION OF THE INVENTION

The invention in its broadest aspects relates to substituted thienopyrans which are useful as antihypertensives. Several of the intermediates used to make the thienopyrans are also novel compounds and are considered to be part of the invention.

The substituted thienopyrans of this invention are prepared as outlined in Scheme 1.

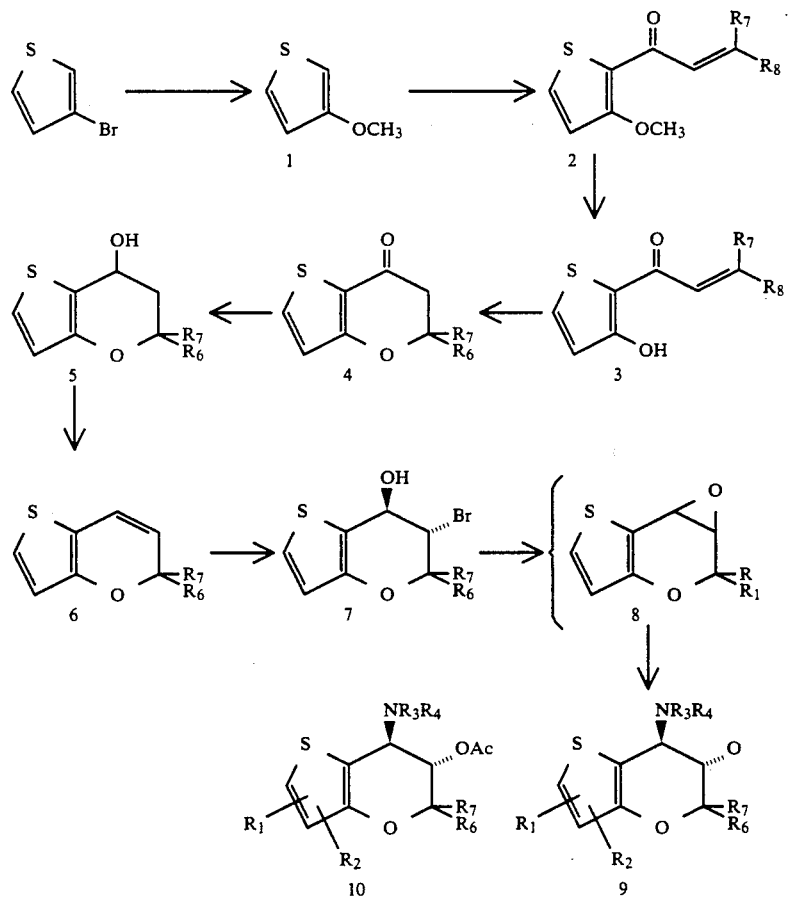

SCHEME 1

SCHEME 1 -continued

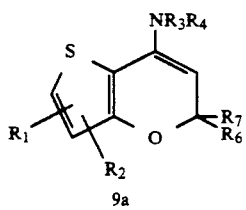

9a

As can be seen from Scheme 1, 3-methoxythiophene (1) prepared from 3-bromothiophene [S. Gronowitz, Arkiv. Kemi., 1958, 12, 239,] is treated with 3,3-disubstituted acryloyl chloride and a Lewis acid catalyst such as tin (IV) chloride, ferric chloride, zinc chloride or the like in an inert solvent such as methylene chloride, chloroform or THF at 0°-25° C. for 1-24 h to give the unsaturated ketone derivative 2. The methoxy group on 2 is cleaved by the action of agents such as boron trifluoride, boron tribromide, boron trichloride, pyridinium hydrochloride or trimethylsilyl iodide in an inert solvent such as methylene chloride or chloroform at −20° to 200° C. to give the alcohol 3. Treatment of 1 with protic acids such as p-toluenesulfonic acid in an inert solvent such as benzene, toluene or the like at reflux temperatures gives the 5,5-disubstituted thieno[3,2-b]pyran-7-one 4. Reduction of the ketone (4) by reducing agents such as sodium borohydride, lithium aluminum hydride or the like in suitable solvents such as alcohols or THF yields the alcohol 5. Dehydration of 5 under acid conditions (p-toluenesulfonic acid, for example) at −20° to 20° C. with molecular sieves in an inert solvent such as dichloromethane, THF or benzene to remove water gives the olefin 6. Alternatively, the ketone (4) may be reduced and the crude, unisolated alcohol (5) may be directly converted to the olefin (6) under similar conditions. Conversion of the olefin (6) to the bromohydrin (7) is accomplished by the action of N-bromosuccinimide and water in solvents such as DMSO or DMF at 0° to 50° C. The bromohydrin (7) is used generally without isolation and treated with bases such as sodium hydride or sodium hydroxide in solvents such as DMSO or DMF at −20° to 200° C. to form the unstable epoxide (8). Alternatively olefin 6 can be converted directly to the epoxide (8) using peracids such as m-chloroperbenzoic acid or pertrifluoroacetic acid in solvents such as aliphatic alcohols or dichloromethane. Anions of amine or amide derivatives are prepared in situ by treating various amines such as pyrrolidine or piperidine or amides such as pyrrolidinone, piperidinone, caprolactam, benzamide and substituted benzamides such as p-nitrobenzamide with sodium hydride in solvents such as DMF or DMSO at room temperature. The epoxide (8) in solvents such as DMF, DMSO or the like is then treated with the thus-formed amine or amide anions at 0° to 20° C. for 1-8 days to form (R$_1$R$_2$ =H). Reaction of 9 with electrophiles such as bromine or nitric acid or the like gives the corresponding substituted thienopyran (9) wherein R$_1$R$_2$=bromine or nitro, for example. When the electrophile is an acylating agent such as, for example, acetyl chloride or acetic anhydride and the reaction is carried out in the presence of a Lewis acid or protic acid catalyst at about −20° to 20° C. for about 1 hour to 6 days, the product is the acyloxy derivative (10) (R$_1$R$_2$=H). Similar reactions with the appropriate electrophile under similar conditions produces the acyl acetate (10) (R$_1$ or R$_2$=acyl, for example, acetyl). Reaction of the acetate 10 with methanolic sodium hydroxide or sodium carbonate at about 0°-250° C. for 1-24 hours yields (R$_1$ or R$_2$=acyl, for example, acetyl).

Reaction of 9 with bases such as sodium hydride in solvents such as THF, DMF or the like at 40°-150° C. for 1-16 hours produces enamine (9a). Alternatively, epoxide 8 is reacted with sodium azide in polar solvents such as DMF or DMSO at about −20° to 100° C. to give azide (NR$_3$R$_4$=N$_3$). Reduction of the azide with typical hydride reducing agents such as lithium aluminum hydride or sodium borohydride in solvents such as diethyl ether, tetrahydrofuran or alcohols at about 0° to 100° C. or with metals such as zinc or iron in acetic acid or dilute hydrochloric acid gives the corresponding aminoalcohol 9(R$_3$,R$_4$=H). Reaction of this amine with acylating agents such as acetyl chloride, benzoyl chloride or substituted benzoyl chlorides, for example, gives the compounds of the invention 9 wherein R$_3$ or R$_4$ is an acyl group such as acetyl, benzoyl or substituted benzoyl.

Treatment of 9 (R$_1$ or R$_2$=Br) with an inorganic or organometallic agent such as palladium dichloride, bis(-triphenylphosphine)palladium chloride or palladium diacetate in an alcoholic solvent such as methanol, ethanol or propanol in the presence of carbon monoxide at temperatures between 25°-1500° C. gives 9 (R$_1$ or R$_2$ =CO$_2$R where R=Me, Et, Pr). Reaction of 9 (R$_1$ or R$_2$=CO$_2$R where R=Me, Et, Pr) with ammonia, ammonium chloride or ammonium hydroxide in an alcoholic solvent such as methanol, ethanol or propanol at a temperature between 0°-50° C. for 1-10 days gives 9 (R$_1$or R$_2$ =CONH$_2$). Treatment of 9 (R$_1$ or R$_2$=CONH$_2$) with dehydrating agents such as trifluoroacetic anhydride produces 9 (R$_1$ or R$_2$=CN).

The thieno[2,3-b]pyran compounds of this invention are prepared according to Scheme 2. As can be seen from the reaction scheme, 2,3-dibromo thiophene is converted by literature procedures [Tetrahedron, 1965, 21, 3331] to 2-t-butoxy-3-bromothiophene which is then treated with t-butyl lithium followed with a 3,3-disubstituted acryloyl acid derivative such as the methyl or ethyl ester, acid chloride, anhydride or amide derivatives at about −700° to 50° C. to give 11. Removal of the t-butyl group and ring closure is done by heating 11 in an inert solvent such as benzene, toluene or xylenes in the presence of catalytic amounts of acids such as p-toluenesulfonic acid to give the 6,6-dimethyl-4H-thieno[2,3-b]pyran-4-one (12).

SCHEME 2

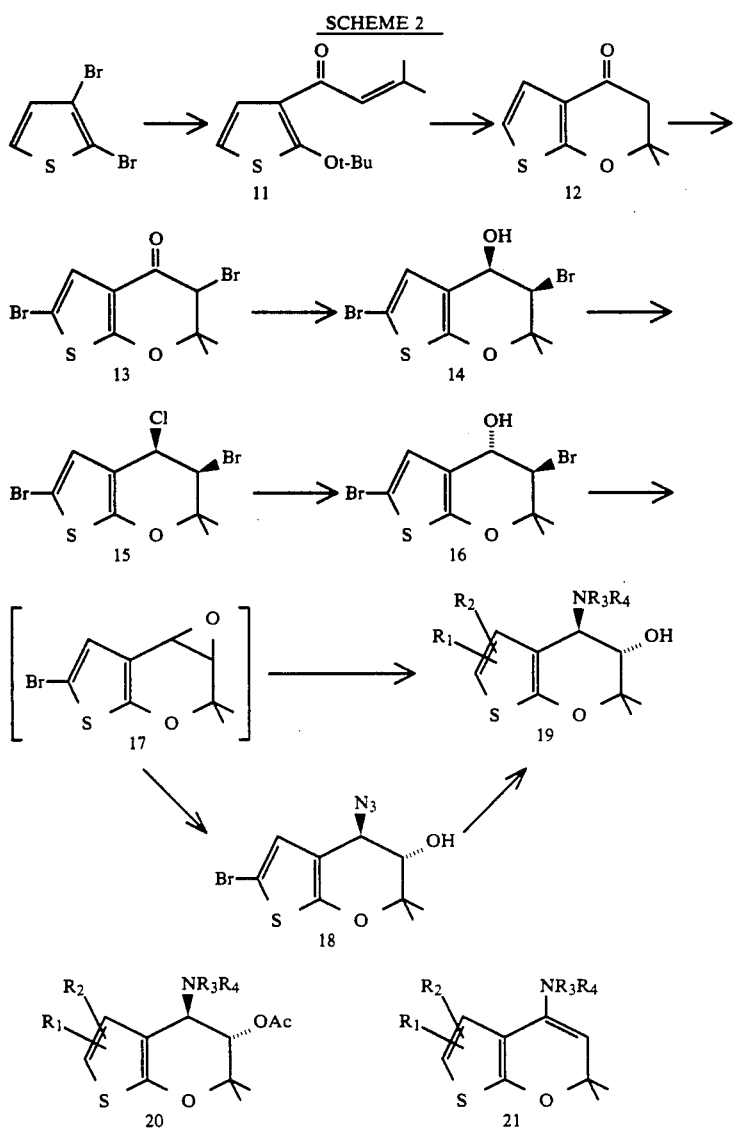

Compound 12 is brominated in an inert solvent such as methylene chloride, chloroform or THF at about 0° to 25° C. for about 1-24 h to give the 2,5-dibromo-6,6-dimethyl-4H-thieno [2,3-b]pyran-4-one (13). Compound 13 is converted to the cis-bromohydrin (14) using lithium aluminum hydride or triphenylphosine in inert solvents such as diethyl ether, THF or toluene at about 0° to 25° C. Compound 14 is treated with a chlorinating agent such as thionyl chloride in an inert solvent such as methylene chloride, chloroform or THF at about 0° to 25° C. for about 1-24 h to give 15. Compound 15 is converted to the trans-bromohydrin 16 upon treatment with "wet" silica gel. The unstable epoxide 17 is formed under basic conditions. Anions of amine or amide derivatives are prepared in situ by treating various amines such as pyrrolidine or piperidine or amides such as pyrrolidinone, piperidinone, pyridinone, caprolactam, benzamide and substituted benzamides such as p-nitrobenzamide with sodium hydride. Epoxide 17 is treated with the thus-formed amine or amide anions to form 19 ($R_1$=Br, $R_2$=H). Reaction of 19 with bases such as sodium hydride in solvents such as THF, DMF or the like at 40° to 150° C. for 1-16 hours produces enamine (21).

Alternatively in a manner analogous to Scheme 1, epoxide 17 is reacted with sodium azide to give azide 18 ($NR_3R_4$=$N_3$). Reduction of the azide with typical hydride reducing agents such as lithium aluminum hydride or triphenylphosphine in solvents such as diethyl ether, THF or toluene or sodium borohydride in aliphatic alcohols at about 0° to 100° C. or with metals such as zinc or iron in acetic acid or dilute hydrochloric acid gives the corresponding aminoalcohol 19 ($R_1$, $R_2$, $R_3$, $R_4$=H). Reaction of this amine with acylating agents such as acetyl chloride, benzoyl chloride or substituted benzoyl chlorides, for example, gives the compounds of the invention 19 wherein $R_3$ or $R_4$ is an acyl group such as acetyl, benzoyl or substituted benzoyl.

Reaction of 19 with electrophiles such as bromine, nitric acid or the like gives the corresponding substituted thienopyran (19) wherein $R_1R_2$=bromine or nitro, or the like, for example. When the electrophile is an acylating agent such as, for example, acetyl chloride or acetic anhydride and the reaction is carried out in the presence of a Lewis acid or protic acid catalyst at about −20° to 20° C. for about 1 hour to 6 days, the product is the acyloxy derivative (20) ($R_1R_2$=H). Further reaction with the appropriate electrophile under similar conditions produces the acyl acetate (20) ($R_1$ or $R_2$=acyl, for example, acetyl). Reaction of the acetate 20 with methanolic sodium hydroxide or sodium carbonate at about 0° to 25° C. for 1–24 hours yields 19 ($R_1$ or $R_2$=acyl, for example, acetyl).

Treatment of 19($R_1$, R=Br) with an inorganic or organometallic agent such as palladium dichloride, bis(triphenylphosphine)palladium chloride or palladium diacetate in an alcoholic solvent such as methanol, ethanol or propanol in the presence of carbon monoxide at temperatures between 25° to 150° C. gives 19 ($R_1$, $R_2$ =$CO_2R$ where R=Me, Et, Pr). Reaction of 19 ($R_1$, $R_2$ =CO 2R where R=Me, Et, Pr) with ammonia, ammonium chloride or ammonium hydroxide in an alcoholic solvent such as methanol, ethanol or propanol at a temperature between 0° to 50° C. for 1–10 days gives 19 ($R_1$, $R_2$ =$CONH_2$). Treatment of 19($R_1$, $R_2$=$CONH_2$) with dehydrating agents such as trifluoroacetic anhydride produces 19 ($R_1$,$R_2$=CN).

The thieno[3,4-b]pyrans are prepared according to Scheme 3. In this reaction sequence, 3,4-dibromothiophene is converted by literature procedures [Tetrahedron, 1965, 21, 3331] to 3-bromo-4-t-butoxythiophene (22) which in turn is converted to 3-lithio-4-t-butoxythiophene according to the same literature procedure. Reaction of the 3-lithio compound with a 3,3-disubstituted acryloyl acid derivative such as the methyl or ethyl ester, acid chloride, anhydride or amide derivatives at about −700° to 50° C. gives the unsaturated ketone derivative (23). Reaction of 23 with protic acid catalysts such as p-toluenesulfonic acid, sulfuric acid or the like at about 50°-250° C. neat or in inert solvents such as toluene or xylenes gives the ring-closed thieno[3,4-b]pyranone derivative (24). Bromination of 24 in a solvent such as methylene chloride, chloroform or THF at 0 to about 25° C. for about 1–24 hours gives the 3-bromo-5,5-dimethylthieno[3,4-b]pyran-7-one (25). Using reaction conditions essentially as those described for Scheme 1, reduction of the ketone gives the alcohol 26 which is dehydrated to give the olefin 27. Treatment of the olefin (27) with N-bromosuccinimide and water in polar solvents gives the bromohydrin 28 which is converted to the epoxide 29. In a manner analogous to that described for Scheme 1, the epoxide 29 may also be reacted with sodium azide in polar solvents to give the azido alcohol 30 ($NR_3R_4$=$N_3$). This azide is reduced with reducing agents such as hydrides or metals in protic acids to give the aminoalcohol 22 ($R_3$,$R_4$=H). Reaction of this amine with acylating agents such as acetyl chloride, benzoyl chloride or substituted benzoyl chlorides, for example, gives the compounds of the invention 30 wherein $R_3$ or $R_4$ is an acyl group such as acetyl, benzoyl or substituted benzoyl.

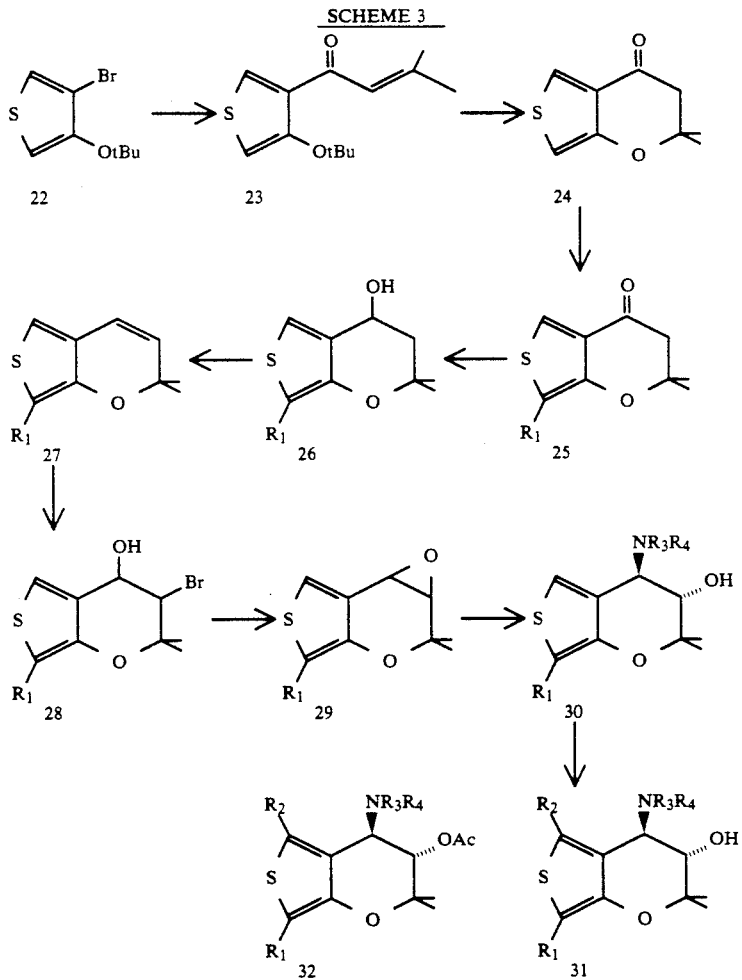

SCHEME 3

Alternatively olefin 27 can be converted directly to the epoxide 29 using peracids such as m-chloroperbenzoic acid or pertrifluoroacetic acid in solvents such as aliphatic alcohols or dichloromethane. Reaction of 29 with the anions of various amines and amides gives the aminoalcohols 30 ($R_1R_2=H$). Reaction of these derivatives with electrophiles such as bromine, chlorine, sulfuryl chloride or nitric acid gives the substituted derivatives 30 ($R_1$ or $R_2=Br$, Cl, $NO_2$), respectively. When the electrophile is an acylating agent such as acetyl chloride or acetic anhydride and Lewis or protic acid catalysis is employed, the product is the acetyl acetoxy derivative 32 ($R_1$ or $R_2=$acetyl) which may be converted to the aminoalcohol 30 ($R_1$ or $R_2=$acetyl) by treatment with alcoholic base.

Those compounds wherein $R_7,R_8=$cycloalkyl can be prepared by reacting a cyclic ketone with a Wittig phosphonium ylide reagent to form the 3,3-cycloalkylidine carboxylic acid which is the acrylic acid component of the starting material used to prepare those compounds wherein $R_7,R_8=$cycloalkyl.

Reaction of 30 with bases such as sodium hydride in solvents such as THF, DMF or the like at 40°–150° C. for 1–16 hours produces the corresponding enamine.

Treatment of 30 ($R_1$ or $R_2=Br$) with an organometallic agent such as palladium dichloride, bis(triphenylphosphine) palladium chloride or palladium diacetate in an alcoholic solvent such as methanol, ethanol or propanol in the presence of carbon monoxide at temperatures between 25°–150° C. gives 30 ($R_1$ or $R_2=CO_2R$ where R=Me, Et, Pr). Reaction of 30 ($R_1$ or $R_2=CO_2R$ where R=Me, Et, Pr) with ammonia, ammonium chloride or ammonium hydroxide in an alcoholic solvent such as methanol, ethanol or propanol at a temperature between 0°–500° C. for 1–10 days gives 30 ($R_1$ or $R_2=CONH_2$). Treatment of 30 ($R_1$ or $R_2=CONH_2$) with dehydrating agents such as trifluoroacetic anhydride produces 30 ($R_1$ or $R_2=CN$). Treatment of U as before with mild bases produces 31.

Reduction of (Scheme 1, $R_1$ or $R_2=NO_2$) by catalytic hydrogenation using typical catalysts such as palladium on carbon in the presence of an acylating agent such as acetic anhydride, or benzoyl chloride, for example, in suitable solvents such as acetic acid, for example, yields 9 ($R_1$ or $R_2=NHR$, R=acetyl, benzoyl). In a similar fashion, the reduction of 9 (Scheme 2, $R_1$ or $R_2=NO_2$) and 31 (Scheme 3, $R_1$ or $R_2=NO_2$) yields the corresponding amide.

Although the cis and trans isomers are formed during the reaction sequence, the product which is isolated is essentially the trans isomer.

Those compounds wherein M is nitrogen are prepared by treating a 3-methoxythiophene (1) with a 2-chloro-2,2-disubstituted acyl halide such 2-chloro-2,2-dimethylacetyl chloride, for example, and a Lewis acid catalyst such as tin (IV) chloride, ferric chloride, zinc chloride or the like in an inert solvent such as methylene chloride, chloroform or THF, for example, at a temperature between OIC and 250° C. for about 1–24 hours to give a ketone derivative. The alkoxy group may be cleaved by the action of agents such as boron trifluoride, boron tribromide, boron trichloride, pyridinium hydrochloride or trimethylsilyl iodide, for example, in an inert solvent such as benzene, toluene or the like, preferably at reflux temperatures, and ring closed by treatment with bases such as DBU (diazabicycloundecane), DBN (diazabicyclononane) or potassium t-butoxide to give a 5,5-disubstituted thieno [3,2]-dihydrofuran-6-one. A Schmidt rearrangement to the thieno [3,2]-bloxazinone can be achieved by treating the ketone with sodium azide in the presence of sulfuric acid and toluene. Alternatively, the ketone can be reacted with hydroxylamine hydrochloride and pyridine in an alcoholic solvent such as reethanol or ethanol to produce the oxime derivative which will undergo a Beckman rearrangement to the thieno [3,2-b] oxazinone in acids such as polyphosphoric acid. The 5,5-disubstituted-7-halothieno [3,2-b] oxazines can be prepared from the lactam by treating it with a halogenating agent such as phosphorus trichloride or phosphorus pentachloride. Reaction of the iminohalide with the anion of an amine or an amide will yield a 5,5-disubstituted-7-(substituted amino) thieno [3,2-b] oxazine. Alternatively, the thieno [3,2-b]oxazinone can be reacted with phosphorus pentasulfide, a base such as sodium methoxide and then with an alkylating agent such as methyl iodide or dimethyl sulfate, for example, to give an alkylthio imino ether which can be reacted with an anion of an amine or an amide to give a 5,5-disubstituted-7-(substituted amino) thieno [3,2-b] oxazine.

Those compounds wherein M is CH and $R_5$ and $R_6$ constitute a double bond can be prepared by treating those compounds wherein $R_6$ is hydroxyl with a base such as sodium hydride in an inert solvent such as THF to form the enamide. Those compounds wherein M is carbonyl are prepared by oxidizing the enamide prepared above with an oxidizing agent such as m-chloroperbenzoic acid and rearranging the epoxide which forms with an acid to form the ketonic compounds.

The compounds of this invention have antihypertensive activity as determined in spontaneously hypertensive rats (SHR). The compounds also have effects on potassium ion permeability changes within smooth muscle cells as determined in the $Rb^{86}$ efflux assay. [J. M. Smith, A. A. Sanchez and A. W. Jones, Blood vessels, 1986, 23, 297]

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral, parenteral or transdermal. In preparing the compositions in oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions ; or carriers such as starches, sugars, diluents, granulating agents, lubricants, binders, disintegrating agents and the like in the case of oral solid preparations such as, for example, powders, capsules, and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain, dosage unit, e.g., tablet, capsule, powder, injection, teaspoonful, aerosol and the like, from about 0.1 to about 100 mg/kg and preferably from about 0.1 to about 20 mg/kg of the active ingredient.

The following examples describe the invention in greater particularity and are intended to be a way of illustrating but not limiting the invention.

BEST MODES OF CARRYING OUT THE INVENTION

Melting point determinations were done on a Thomas Hoover capillary melting point apparatus and are uncorrected. All compounds had spectra (IR, $^1$H NMR, MS) consistent with their assigned structures and were homogeneous by thin layer chromatography. $^1$H NmR were determined on a Brucker WP-100 FT or a GE QE-300 spectrometer. MS were determined on a Finnigan Mat 8230 using desorption chemical ionization techniques. Silica Gel 60, 230-400 mesh, was used for both flash chromatography and medium pressure chromatography.

EXAMPLE 1

3-Methoxy-2-(3-methyl-1-oxo-2-buten-1-yl)thionphene (2)

A solution of 3-methoxythiophene (21.3 g, 0.187 mol) [S. Gronowitz, Arkiv. Kemi., 1958, 12, 239] in dichloromethane (50 mi) was slowly added to a solution of 3,3-dimethylacryloyl chloride (22 mL, 0.195 mol) and tin-(IV) chloride (23 mL, 0.195 mol) in dichloromethane (350 mL) at 0°-5° C. After stirring at 0°-5° C. an additional 1 h, the solution was poured into ice water (1 L). The organic layer was separated, washed with water, and dried over magnesium sulfate. The solvent was evaporated in vacuo. The resulting oil was purified by flash chromatography using dichloromethane as the eluant to give the product, 29.6 g (81%): mp 49°-51° C.; IR (KBr): 1671, 1628 and 1430 cm$^{-1}$; MS: m/z 197 (MH+); $^1$H NMR (CDCl$_3$): δ1.98 (d, J=1.2 Hz, 3H), 2.23 (d, J=1.1 Hz, 3H), 3.98 (s, 3H), 6.85 (d, J=5.5 Hz,1H), 6.89 (dd, J=1.1 Hz, J=1.2 Hz, $^1$H) and 7.47 (d, i=5.5 Hz, $^1$H).

Anal. Calcd. for C$_{10}$H$_{12}$O$_2$S: C, 61.20; H, 6.16; S, 16.34.

Found: C, 61.19; H, 6.17; S, 16.31.

3-Hydroxy-2-(3-methyl-1-oxo-2-buten-1-yl)thionhene (3)

A solution of boron trichloride, (1.0 M in dichloromethane, 800 mL, 0.80 mol) was slowly added to a solution of 3-methoxy-2-(3-methyl-1-oxo-2-buten-1-yl) thiophene (52.3 g, 0.27 mol) in dichloromethane (400 mL) at −10° C. to 5° C. The resultant solution was stirred an additional 1.5 h at −50° C. Ice water was added slowly with rapid stirring. The organic layer was separated, dried over sodium sulfate, and eluted through a pad of silica gel. The solvent was evaporated in vacuo and the resultant oil was crystallized from hexanes at −70° C. to give the product, 40.0 g (82%), as a yellow solid: mp 32°-33° C.; IR (KBr): 1641, 1581 and 1541 cm$^{-1}$; MS: m/z 183 (MH+); $^1$H NMR (CDCl$_3$): w 2.00 (d, J=1.1 Hz, 3H), 2.30 (d, J=1.0 Hz, 3H), 6.25 (m, $^1$H), 6.75 (d, J=5.3 Hz, 1H), 7.37 (d, J=5.3 Hz, $^1$H) and 12.14 (s, exchanges with D$_2$O, 1H).

Anal. Calcd. for C$_9$H$_{10}$O$_2$S: C, 59.32; H, 5.54; S, 17.59.

Found: C, 59.35; H, 5.51; S, 17.62.

5.6-Dihydro-5,5-dimethyl-7H-thieno[3,2-b]pyran-7-one (4)

A solution of 3-hydroxy-2-(3-methyl-1-oxo-2-buten-1-yl) thiophene (39.0 g, 0.214 mol) and p-toluenesulfonic acid (3.5 g, 18 mmol) in toluene (400 mL) was heated to reflux for 3.5 d. The resultant solution was washed with saturated aqueous sodium bicarbonate and dried over sodium sulfate. The solvent was evaporated in vacuo to give a brown oil, 38.62 g (99%). A portion of the resultant oil was purified for analysis by distillation in a Kugelrohr oven at 145° to 155° C. at 0.35 mm Hg to give the product as an amber oil: IR (neat): 2979, 1664, 1530 and 1442 cm$^{-1}$; MS: m/z 183 (MH+); $^1$H NMR (CDCl$_3$) δ1.51 (s, 6H); 2.67 (s, 2H); 6.67 (d, J=5.4 Hz, $^1$H) and 7.60 (d, J=5.4 Hz, $^1$H)

Anal. Calcd. for C$_9$H$_{10}$O$_2$S: C, 59.32; H, 5.54; S, 17.69.

Found: C, 59.39; H, 5.53; S, 17.67.

5.6-Dihydro-7-hydroxy-5,5-dimethyl-7H-thieno]3.2-b]pyran (5)

Sodium borohydride (0.97 g, 25.5 mmol) was added to a solution of 5,6-dihydro-5,5-dimethyl-7H-thieno [3,2-b]pyran-7-one (3.1 g, 17.0 mmol) in ethanol (50 mL) and stirred at rt for 2 h. An additional 0.97 g of sodium borohydride was added and the mixture was stirred 16 h. The mixture was poured into water and extracted with dichloromethane. The dichloromethane solution was washed with water (5x) and dried over magnesium sulfate. The solvent was evaporated in vacuo to give the product, 2.96 g (95%), as a brown oil: IR (neat): 3373, 2976, 1561 and 1400 cm$^{-1}$; MS: m/z 185 (MH+); $^1$H NMR (CDCl$_3$) δ 1.34 (s, 3H), 1.45 (s, 3H), 1.87 (m, $^1$H), 1.94 (d, J=7.0 Hz, $^1$H, exchanges with D$_2$O), 2.16 (m, $^1$H), 4.88 (m, 1H), 6.57 (d, J=5.4 Hz, $^1$H), 7.13 (d, J=5.4 Hz, $^1$H). This oil was used without further purification in the next step.

5,5-Dimethyl-5H-thieno]3,2-b]pyran (6, Method A)

A mixture of 5,6-dihydro-7-hydroxy-5,5-dimethyl-7H-thieno [3,2-b]pyran (1.3g, 7.06 mmol), p-toluenesulfonic acid (0.11 g, 0.58 mmol) and ground molecular sieves (1.3 g) was stirred at −5° C. for 1.5 h. The mixture was washed with 1.0 N aqueous sodium hydroxide and dried over magnesium sulfate. The solvent was evaporated in vacuo to give the product, 1.17 g (99%), as a red oil: IR (neat): 2976, 1504 and 1531 cm$^{-1}$; MS: m/z 167 (MH+); $^{11}$H NMR (CDCl$_3$) δ 1.45 (s, 6H), 5.27 (d, J=9.8 Hz, $^1$H), 6.30 (d, J=9.8 Hz, $^1$H), 6.60 (d, J=5.3 Hz, $^1$H) and 6.99 (d, J=5.3 Hz, $^1$H). This oil was used without further purification in the next step.

5.5-Dimethyl-5H-thieno]3,2-b]pyran (6, Method B)

Sodium borohydride (3.27 g, 86.3 mmol) was added to a solution of 5,6-dihydro-5,5-dimethyl-7H-thieno [3,2-b]-pyran-7-one (12.1 g, 66.4 mmol) in ethanol (100 mL) and the resultant mixture was stirred at rt for 17 h. The mixture was poured into water (400 mL) and extracted with dichloromethane (2×100 mL). The dichloromethane solution was washed with water (5x), dried over sodium sulfate, and filtered. Molecular sieves (12 g) and p-toluenesulfonic acid (1.2 g, 6.3 mmol) was added to the resultant solution and stirred at OIC for 1.5 h. The reaction mixture was filtered, washed with saturated aqueous sodium bicarbonate and dried over sodium sulfate. The solvent was evaporated in vacuo to give the product, 11.0 g (99%), as a red oil which was identical in all respects to the product described in Method A.

6-Bromo-7-hydroxy-5,6-dihydro-5,5-dimethyl-7H-thieno]3.2-b]pyran (7)

N-Bromosuccinimide (12.9 g, 72.5 mmol) was added in portions to a solution of 5,5-dimethyl-5H-thieno[3,2-b]pyran (10.95 g, 65.9 mmol) and water (1.6 mL, 89.5 mmol) in dimethyl sulfoxide (110 mL) at rt. The resultant solution was stirred at rt for 16 h poured into ice water (400 mL) and extracted into dichloromethane. The dichloromethane solution was washed with water (5x) and dried over sodium sulfate. The solvent was evaporated in vacuo and the residue was purified by flash chromatography using dichloromethane as the eluant to give the product, 11.5 g (66%), as a brown oil: Note that this oil is thermally unstable and decomposes within several hours at rt: $^1$H NMR (CDCl$_3$) δ 1.44 (s, 3H), 1.60 (s, 3H), 2.56 (d, J=4 Hz, $^1$H, exchanges with D$_2$O), 4.10 (d, J=7 Hz, $^1$H), 4.98 (dd, J=4 Hz, J=7 Hz, $^1$H), 6.56 (d, J=5 Hz, 1H), 7.16 (d, J=5 Hz, $^1$H). This oil was used without further purification in the next step.

5,6-Dihydro-6-hydroxy-5,5-dimethyl-7-(2-oxopyrrolidin-1-yl)-7H-thieno [3,2-b]pyran Sodium hydride (60% in oil, 1.17 g, 29.3 mmol) was added to a solution of 6-bromo-7-hydroxy-5,6-dihydro-5,5-dimethyl-7H-thieno [3,2-b]pyran (7.0 g, 26.6 mmol) in N,N-dimethylformamide (115 mL) at 0° C. The resultant mixture was stirred at rt for 2 h. 2-Pyrrolidinone (6.1 mL, 79.8 mmol) was added to the solution followed by sodium hydride (60% in oil, 1.17 g, 29.3 mmol) and stirring was continued at rt for 4 days. The solution was poured into ice water (500 mL) and extracted with dichloromethane. The dichloromethane solution was washed with water (5x) and dried over sodium sulfate. The solvent was evaporated in vacuo and the resultant solid was triturated in diethyl ether to give the product, 3.91 g (55%), as a colorless solid: mp 154°-155° C.; IR (KBr): 3263, 1665 and 1562 cm$^-$; MS: m/z 268 (MH$^+$); $^1$H NMR (CDCl$_3$) δ 1.30 (s, 3H), 1.50 (s, 3H), 2.07 (m, 2H), 2.52 (m, 2H), 3.00 (d, J=5.5 Hz, $^1$H, exchanges with D$_2$O), 3.35 (m, 2H), 3.78 (dd, J=5.5 Hz, J=9.0Hz $^1$H, simplifies to d, J=9.0 Hz, with D$_2$O), 5.28 (d, J=9.0 Hz, 1H), 6.57 (d, 5.4 Hz, 1H) and 7.11 (d, J=5.4 Hz, $^1$H).

Anal. Calcd. for C$_{13}$H$_{17}$NO$_3$S: C, 58.40; H, 6.41; N, 5.24; S, 11.99.

Found: C, 58.57; H, 6.47; N, 5.23; S, 12.03.

EXAMPLE 2

5,6-Dihydro-6-hydroxy-5,5-dimethyl-7-(2-oxopiperidin-1-yl)-7H-thieno [3,2-b]pyran 6-Bromo-7-hydroxy-5,6-dihydro-5,5-dimethyl-7H-thieno[3,2-b]pyran (1.5 g, 5.7 mmol) and w-valerolactam (1.7 g, 17.1 mmol) were treated with sodium hydride (0.50 g, 12.5 mmol) in N,N-dimethylformamide (25 mL) using the procedure described in Example 1 to give the product as a colorless solid, 0.681 g (43%): mp 151°-152° C.; IR (KBr): 3195, 1610 and 1563 cm$^{-1}$ ; MS: m/z 282 (MH$^+$); $^1$$^1$H NMR (CDCl$_3$) δ 1.29 (s, 3H), 1.49 (s, 3H), 1.81 (m, 4H), 2.53 (t, J=6.5 Hz, 2H), 3.15 (m, $^1$H), 3.24 (m, $^1$H), 3.68 (d, J=5.0 Hz, $^1$H, exchanges with D$_2$O), 3.79 (dd, J=5.0 Hz, J=9.1 Hz, $^1$H, simplifies to d, J=9.1 Hz with D$_2$O), 5.84 (d, J=9.1 Hz, $^1$H), 6.57 (d, J=5.4 Hz, $^1$H) and 7.11 (d, J=5.4 Hz, 1H).

Anal. Calcd. for C$_{14}$H$_{19}$NO$_3$S: C, 59.76; H, 6.81; N, 4.98; S, 11.40.

Found: C, 59.85; H, 7.05; N, 5.11; S, 11.26.

EXAMPLE 3

5,6-Dihydro-6-hydroxy-5,5-dimethyl-7-(4-nitrobenzamido)-7H-thieno [3,2-b]pyran 6-Bromo-7-hydroxy-5,6-dihydro-5,5-dimethyl-7H-thieno-[3,2-b]-pyran (6.8 g, 25.8 mmol) and 4-nitrobenzamide (10.7 g, 64.5 mmol) were treated with sodium hydride 60% in oil (2.26 g, 56.8 mmol) in N,N-dimethylformamide (110 mL) using the procedure described for the preparation of 5,6-dihydro-6-hydroxy-5,5- dimethyl-7-(2-oxopyrrolidin -1-yl)-7H-thieno[3,2-b]pyran. The reaction mixture was poured into water and extracted into 10% isopropanol in dichloromethane. The solvent was evaporated in vacuo and the residue was purified by medium pressure chromatography using 2% methanol in dichloromethane as the eluant to give the product, 4.5 g (50%), as a pale yellow solid: mp 183°-186° C. dec; IR (KBr): 3398, 1664, 1644 and 1601 cm$^{-1}$; MS: m/z 349 (MH$^+$); $^1$$^1$H NMR (CDCl$_3$): w 1.35 (s, 3H), 1.50 (s, 3H), 3.79 (d, J=7.9 Hz, $^1$H), 4.26 (bs, $^1$H, exchanges with D$_2$O), 5.19 (d, d, J=7.9 Hz, and J=7.0 Hz, 1H), 6.59 (bd, J=7.0 Hz, $^1$H, shifts to 6.66 with D$_2$O), 6.63 (d, J=5.4 Hz, $^1$H), 7.18 (d, J=5.4 Hz, $^1$H), 7.97 (d, J=8.8 Hz, 2H) and 8.32 (d, J=8.8 Hz, 2H).

Anal. Calcd. for C$_{16}$H$_{16}$N$_2$O$_5$S: C, 55.16; H, 4.63; N, 8.04; S, 9.20.

Found: C, 55.45; H, 4.76; N, 8.25; S, 9.14.

EXAMPLE 4

2-Bromo-5,6-dihydro-6-hydroxy-5,5-dimethyl-7-(2-oxopyrrolidin-1-yl) -7H-thieno [3.2-b]pyran A solution of bromine (0.20 mL, 3.92 mmol) in dichloromethane (5 mL) was slowly added to a solution of 5,6-dihydro-6-hydroxy-5,5-dimethyl-7-(2-oxopyrrolidin-1-yl)-7H-thieno [3,2-b]pyran (1.0 g, 3.74 mmol) at −5° C. The resultant mixture was stirred at rt for 2 h. The resulting precipitate was collected byfiltration and purified by medium pressure chromatography using 5% methanol in dichloromethane as the eluant to give the product as a colorless solid, 0.28 g (22%): mp 162°-165° C.; IR(KBr): 3287, 1666 and 1570 cm$^{-1}$; MS: m/z 346 (MH$^+$); $^1$H NMR (CDCl$_3$) δ 1.30 (s, 3H), 1.47 (s, 3H), 2.06 (m, 2H), 7.50 (m, 2H), 3.23 (bs, $^1$H, exchanges with D$_2$O), 3.34 (m, 2H), 3.76 (d, J=9.1 Hz, 1H) 5.16 (d, J=9.1 Hz, $^1$H) and 6.56 (s, $^1$H).

Anal. Calcd. for C$_{13}$H$_{16}$BrNO$_3$S: C, 45.10; H, 4.66; N, 4.05.

Found: C, 45.10; H, 4.40; N, 3.97.

EXAMPLE 5

5,6-Dihydro-6-hydroxy-5,5-dimethyl-2-nitro-7-(2-oxopyrrolidin-1-yl) -7H-thieno [3,2-b]pyran Nitric acid (90%, 1.2 mL, 26.9 mmol) was added to a solution of 5,6- dihydro-6-hydroxy-5,5-dimethyl-7-(2-oxopyrrolidin-1-yl) -7H-thieno[3,2-b]pyran (1.0 g, 3.74 mmol) in acetic acid (30 mL) at 18° C., and stirred at rt for 1.5 h. The resultant solution was poured into ice water (200 mL). Within 10 min a yellow solid crystallized which was collected by filtration, washed with water and triturated in diethyl ether to give the product, 0.487 g (42%), as a yellow solid: mp 214°-217° C.; IR (KBr): 3216, 1655 and 1512 cm$^{-1}$; MS: m/z 313 (MH$^+$); $^1$$^1$H NMR (DMSO-d$_6$): w 1.23 (s, 3H), 1.43 (s, 3H), 2.00 (m, 2H), 2.36 (m, 2H), 3.16 (m, 1H), 3.20 (m, 1H), 3.80 (d, J=9.5 Hz, 1H), 4.98 (d, J=9.5 Hz, 1H), 5.92 (bs, 1H, exchanges with $D_2O$) and 7.75 (s, 1H).

Anal. Calcd. for $C_{13}H_{16}N_2O_5S$: C, 49.99; H, 5.16; N, 8.97; S, 10.27.

Found: C, 49.70; H, 5.00; N, 8.65; S, 10.33.

EXAMPLE 6

6-Acetoxy-2-acetyl-5,6-dihydro-5,5-dimethyl-5-(2-oxopyrrolid-1-yl) -7H-thieno [3,2-b]]pyran A solution of 5,6-dihydro-6-hydroxy-5,5-dimethyl-7(2-oxopyrrolidin-1-yl) - 7H-thieno[3,2-b]pyran (1.76 g, 6.58 mmol) and perchloric acid (70%, 10 drops) in acetic anhydride (15 ML) was stirred at 60° C. for 2 h. The resultant brown solution was poured into ice water (100 mL) and the product was extracted into dichloromethane, washed with water (4x) and dried over sodium sulfate. The solvent was evaporated in vacuo and the resultant oil was purified by medium pressure chromatography using 1% methanol in dichloromethane as the eluant to give the product, 0.85 g (37%): mp 170°-172° C.; IR (KBr): 1755, 1690, 1666 and 1564 cm$^{-1}$; MS: m/z 352 (MH+); 1H NMR (CDCl$_3$): w 1.38 (s, 3H), 1.39 (s, 3H), 1.98 (m, 2H), 2.10 (s, 3H), 2.37 (m, 2H), 2.49 (s, 3H), 3.23 (m, 1H), 3.38 (m 1H), 5.14 (d, J=9.3 Hz, 1H), 5.47 (d, J=9.3 Hz, 1H) and 7.16 (s, 1H).

Anal. Calcd. for $C_{17}H_{21}NO_5S$: C, 58.10; H, 6.02; N, 3.99; S. 9.12.

Found: C, 57.76; H, 5.87; N, 3.69; S, 9.11.

EXAMPLE 7

2-Acetyl-5,6-dihydro-6-hydroxy-5,5-dimethyl-7-(2-oxopyrrolidin-1-yl) -7H-thieno [3,2-b]pyran Aqueous sodium hydroxide (50%, 0.15 g, 1.87 mmol) was added to a solution of 6-acetoxy-2-acetyl-5,6-dihydro-5,5-dimethyl-7-(2-oxopyrrolidin-1-yl)-7H-thieno[3,2-b]pyran (0.45 g, 1.28 mmol) in methanol (20 mL) and stirred at rt for 1h. The solution was poured into water (100 mL) and extracted into dichloromethane. The dichloromethane solution was washed with water (3x) and dried over magnesium sulfate. The solvent was evaporated in vacuo and the resultant oil was crystallized from diethyl ether and hexanes to give the product, 0.327 g (83%), as a colorless solid: mp 102°-106° C.; IR (KBr): 1665 and 1561 cm$^{-1}$; MS: m/z 310 (MH+); 1H NMR (CDCl$_3$) w 1.31 (s, 3H), 1.51 (s, 3H), 2.07 (m, 2H), 2.48 (s, 3H), 2.51 (m, 2H), 3.34 (m, 2H), 3.45 (d, J=6.2 Hz, 1H, exchanges with $D_2O$), 3.80 (dd, J=6.2 Hz and J=9.4 Hz, 1H, simplifies to d, J=9.4 Hz, with $D_2O$), 5.29 (d, J=9.4 Hz, 1H) and 7.14 (s, 1H).

Anal. Calcd. for $C_{15}H_{19}NO_4S$: C, 58.23; H, 6.19; N, 4.53.

Found: C, 58.30; H, 6.31; N, 4.45.

EXAMPLE 8

6-Acetoxy-5,6-dihydro-5,5-dimethyl-7-(2-oxopyrrolidin-1-yl) -7H-thieno[3,2-b]pyran A solution of 5,6-dihydro-6-hydroxy-5,5-dimethyl-7-(2-oxopyrrolidin-1-yl)-7H-thieno[3,2-b]pyran (2.0 g, 7.48 mmol) and perchloric acid (70%, 10 drops) in acetic anhydride (20 mL) were stirred for 1 h at 0°-5° C. The solution was poured into ice water (100 mL). The product was extracted into dichloromethane, washed with water (4x), and evaporated in vacuo. The resultant oil was purified by flash chromatography, using 1% methanol in dichloromethane as the eluant, then crystallized from hexanes to give the product, 2.12 g (92%), as a colorless solid: mp 92°-93° C.; IR(KBr): 1745 and 1684 cm$^{-1}$; MS: 310 (MH+); 1H NMR (CDCl$_3$): w 1.37 (s, 3H), 1.38 (s, 3H), 1.98 (m, 2H), 2.10 (s, 3H), 2.37 (m, 2H), 3.24 (m, 1H), 3.40 (m, 1H), 5.15 (d, J=9.1 Hz, 1H), 5.44 (d, J=9.1 Hz, 1H), 6.58 (d, J=5.4 Hz, 1H) and 7.13 (d, J=5.4 Hz, 1H).

Anal. Calcd. for C H NO S: C, 58.23; H, 6.19; N, 4.52; S, 10.36.

Found: C, 58.11; H, 5.89; N, 4.31; S, 10.41.

EXAMPLE 9

5,6-Dihydro-6-hydroxy-5,5-dimethyl-2-nitro-7-(4-nitrobenzamido) -7H-thieno]3,2-b]pyran 5,6-Dihydro-6-hydroxy-5,5-dimethyl-7-(4-nitrobenzamido)-7H-thieno [3,2-b]pyran (1.5 g, 4.30 mmol) was treated with 90% nitric acid (2.5 mL, 53.5 mmol) in acetic acid (25 mL) and stirred at 15°-20° C. for 0.5 h. The resultant solution was poured into ice water 100 mL and extracted with 10% isopropanol in dichloromethane. The dichloromethane solution was washed with saturated aqueous sodium bicarbonate and dried over magnesium sulfate. The solvent was evaporated in vacuo and the residue was purified by medium pressure chromatography using 2% methanol in dichloromethane as the eluant, to give the product, 0.489g (29%), as a yellow solid: mp 221°-225° C. dec; IR (KBr): 3345, 1647 and 1602 cm$^1$; MS: m/z 394 (MH+); 1H NMR (DMSO-d$_6$): w 1.26 (s, 3H), 1.45 (s, 3H), 3.90 (dd, J=8.8 Hz and J=5.9 Hz, 1H, simplifies to d, J=8.8 Hz with $D_2O$), 4.98 (dd, J=7.6 Hz and J=8.8 Hz, 1H, simplifies to d, J=8.8 Hz with D 20), 6.01 (d, J=5.9 Hz, 1H exchanges with D 0), 7.75 (s, 1H), 8.14 (d, J=8.8 Hz, 2H) 8.37 (d, J=8.8 Hz, 2H) and 9.38 (d, J=7.6 Hz, 1H, exchanges with $D_2O$).

Anal. Calcd. for $C_{16}H_{15}N_3O_7S$: C, 48.85; H, 3.84; N, 10.68.

Found: C, 48.91; H, 3.62; N, 10.46.

EXAMPLE 10

5,6-Dihydro-6-hydroxy-5,5-dimethyl-2-nitro-7-(2-oxopiperidin-1-yl) -7H-thieno]3,2-b]pyran The title compound was prepared as described in Example 5 starting with 5,6-dihydro-6-hydroxy-5,5-dimethyl-7-(2-oxopiperidin-1-yl)-7 H-thieno[3,2-b]pyran (1.5 g, 5.33 mmol) and 90% nitric acid (2.5 mL) in acetic acid (25 mL) to give the product, 0.837 g (48%), as a yellow solid: mp 210°-211 ° C.; IR (KBr): 3231, 1613, 1515 and 1492 cm$^{-1}$; MS: m/z 327 (MH+) 1H NMR (CDCl$_3$): δ1.32 (s, 3H), 1.51 (s, 3H), 1.84 (m, 4H), 2.55 (m, 2H), 3,20 (m, 2H), 3.84 (d, J=9.5 Hz, 1H), 4.78 (bs, 1H, exchanges with $D_2O$), 5.86 (d, J=9.5 Hz, 1H) and 7.40 (s, 1H).

Anal. Calcd. for $C_{14}H_{18}N_2O_5S$: C, 51.52; H, 5,56; N, 8.58; S, 9.86.

Found: C, 51.26; H, 5.25; N, 8.32; S, 9.86.

EXAMPLE 11

2-Bromo-5,6-dihydro-6-hydroxy-5,5-dimethyl-7-(2-oxopiperidin-1-yl) -7H-thieno]3,2-b]pyran The title compound was prepared as described in Example 4 starting with 5,6-dihydro-6-hydroxy-5,5-dimethyl-7-(2-oxopiperidin-1-yl) -7H-thieno[3,2-b]pyran (1.4 g, 5.0 mmol) and bromine (0.27 mL, 5.2 mmol) in dichloromethane (30 mL). Purification by flash chromatography using 1% methanol in dichloromethane as the eluant and recrystallization from dichloromethane/- hexanes gave the product, 3.87 g (78%), as a colorless solid: mp 200°-202 C; IR(KBr): 3442, 2942, 1616, 1571 and 1488 cm$^{-1}$; MS: m/z 360 (MH+); $^1$H NMR(CDCl$_3$): δ 1.29 (s, 3H), 1.46 (s, 3H), 1.82 (m, 4H), 2.51 (m, 2H), 3.12 (m, $^1$H), 3,27 (m, $^1$H), 3.46 (d, J=5.0 Hz, $^1$H, exchanges with D$_2$O),3.78 (d,d, J=9.0 Hz, J=5.0 Hz,1H, simplifies to d, J=9.0 Hz, with D$_2$O), 5.74 (d, J=9.0 Hz, $^1$H) and 7.58 (s, $^1$H).

Anal. Calcd. for C$_{14}$H$_{18}$BrNO$_3$S: C, 46.67; H, 5.04; N, 3.89.

Found: C, 46.99; H, 5.05; N, 3.84.

EXAMPLE 12

6-Acetoxy-2-acetyl-5,6-dihydro-5,5-dimethyl-7-(4-nitro-benzamido) -7H-thieno]3,2-b]pyran The title compound was prepared as described in Example 6 starting with 5,6-dihydro-6-hydroxy-5,5-dimethyl-7-4-nitrobenzamido) -7H-thieno[3,2-b]pyran (1.5 g, 4.31 mmol), acetic anhydride (15 mL) and perchloric acid (70%, 10 drops) to give the product, 0.86 g (46%), as a pale yellow solid: mp 251°-253° C. dec; IR (KBr): 1753, 1670, 1655 and 1530 cm$^{-1}$; MS: m/z 433 (MH+) $^1$H NMR (CDCl$_3$): w 1.41 (s, 3H), 1.44 (s, 3H), 2.14 (s, 3H), 2.48 (s, 3H), 5.18 (d, J=9.3 Hz, $^1$H), 5.40 (d,d, J=8.3 Hz, J=9.3 Hz, $^1$H), 6.83 (d, J=8.3 Hz, $^1$H, shifts to d 6.91 with D$_2$O), 7.14 (s, $^1$H); 7.94 (d, J=7.1 Hz, 2H), 8.30 (d, J =7.1 Hz, 2H).

Anal. Calcd. for C$_{20}$H$_{20}$N$_2$O$_7$S: C, 55,55; H, 4.66; N, 6.48; S, 7.41.

Found: C, 55.34; H, 4.69; N, 6.44; S, 7.31.

EXAMPLE 13

2-Acetyl-5,6-dihydro-6-hydroxy-5,5-dimethyl-7-(4-nitrobenzamido) -7H-thieno[3,2-b]pyran 6-Acetoxy-2-acetyl-5,6-dihydro-5,5-dimethyl-7-(4-nitro-benza mido)-7H-thienopyran (0.60 g, 1.39 mmol) was treated with aqueous sodium hydroxide (1N, 1.5 mL, 1.5 mmol) in methanol (10 mL) at rt and stirred for 2 h. The resultant solution was poured into water and extracted with 5% isopropanol in dichloromethane. The organic phase was washed with water (3x) and dried over magnesium sulfate. The solvent was evaporated in vacuo and the resultant solid triturated in diethyl ether to give the product, 0.36 g (66%), as a pale yellow solid: mp 223°-225° C.; IR (KBr): 1647, 1601, 1530 and 1458 cm$^{-1}$; MS: m/z 391 (MH+);$^1$H NMR (DMSO-d$_6$): w 1.23 (s, 3H), 1.42 (s, 3H), 2.45 (s, 3H), 3.84 (m, $^1$H, simplifies to d, J=8.9 Hz with D$_2$O), 5.01 (m, $^1$H, simplifies to d, J=8.9 Hz, with D$_2$O), 5.86 (d, J=5.9 Hz, 1H, exchanges with D$_2$O), 7.47 (s, $^1$H), 8.14 (d, J=8.8 Hz, 2H), 8.36 (d, J=8.8 Hz, 2H) and 9.27 (d, $^1$H, exchanges with D$_2$O).

Anal. Calcd. for C$_{18}$H$_{18}$N$_2$O$_6$S: C, 55.38; H, 4.65; N, 7.18; S, 8.21.

Found: C, 55.12; H, 4.63; N, 6.93; S, 8.11.

EXAMPLE 14

7-(4-Chlorobenzamido)-5,6-dihydro-6-hydroxy-5,5-dimethyl -7H-thieno[3,2-b]pyran

The title compound was prepared as described in Example 3 starting with 6-bromo-7-hydroxy-5,6-dihydro-5,5-dimethyl -7H-thieno[3,2-b]pyran (4.75g, 18.1 mmol) and 4-chlorobenzamide (7.0 g, 45 mmol) in N,N-dimethylformamide (125 mL) to give 1.41 (23%) as a yellow solid: mp 196°-197° C.; IR (KBr): 3483, 3317, 1632 and 1525 cm MS: m/z 338 (MH+);$^1$$^1$H NMR (DMSO-D ): w 1.20 (s, 3H), 1.39 (s, 3H), 3.79 (m, $^1$H, simplifies to d, J=8.8 Hz, with D$_2$O), 4.98 (m, 1H, simplifies to d, J=8.8 Hz with D$_2$O), 5,64 (d, J=6.0 Hz, $^1$H, exchanges with D$_2$O), 6.58 (d, J=5.3 Hz, $^1$H), 7.29 (d, J=5.3 Hz, $^1$H), 7.56 (d, J=6.8 Hz, 2H), 7.93 (d, J=6.8 Hz, 2H) and 8.88 (d, J=8.3 Hz, $^1$H, exchanges with D$_2$O).

Anal. Calcd. for C H CLNO S: C, 56.89; H, 4.77; N, 4.15.

Found: C, 56.72; H, 4.68; N, 4.00.

EXAMPLE 15

7-(4-Chlorobenzamido)-5,6-dibydro-6-hydroxy-5,5-dimethyl-2-nitro-7H-thieno]3,2-b]pyran The title compound was prepared as described in Example 9 starting with 7-(4-chlorobenzamido)-5,6-dihydro-6-hydroxy-5,5-dimethyl-7H-thieno[3,2-b]pyran (1.23 g, 3.64 mmol) and nitric acid (1.5 mL) in acetic acid (20 mL) to give the product, 0.384 g (28%), as a yellow solid: mp 6°-229° C. dec; IR (KBr): 3315, 1655, 1535 and 1503 cm$^{-1}$; MS: m/z 383 (MH+);1$^1$H NMR (DMSO-d$_6$): w 1.25 (s, 3H), 1.44 (s, 3H), 3.90 (m, $^1$H, simplifies to d, J=8.9 Hz with D$_2$O), 4.95 (m, 1H, simplifies to d, J=8.9 Hz, with D$_2$O), 5.94 (d, J=6.0 Hz, $^1$H exchanges with D$_2$O), 7.60 (d, J=8.6 Hz, 2H), 7.72 (s, $^1$H), 7.94 (d, J =8.6 Hz, 2H) and 9.11 (d, J=7.6 Hz, $^1$H, exchanges with D$_2$O).

Anal. Calcd. for C$_{16}$H$_{15}$ClN$_2$O$_5$S: C, 50.20; H, 3.94; N, 7.32; Cl,9.61; S, 8.69.

Found: C, 50.34; H, 3.75; N, 7.00; Cl, 9.36; S, 8.74.

EXAMPLE 16

5,6-Dihydro-6-hydroxy-5,5-din (4-trifluoromethylbenzamido) -7H-thieno]3,2-b]pyran The title compound was prepared as described in Example 3 starting with 6-bromo-7-hydroxy-5,6-dihydro-5,5-dimethyl-7H-thieno [3,2-b]pyran (4.5 g, 17.1 mmol) and 4-trifluoromethylbenzamide (7.43 g, 39.3 mmol) in N,N-dimethylformamide (75 mL) to give the product, 1.96g (31%), as a colorless solid: mp 162°-163° C.; IR (KBr): 3396, 1664, 1534 and 1507 cm$^{-1}$; MS: m/z 372 (MH+); 1H NMR (DMSO-d$_6$): w 1.21 (s, 3H), 1.40 (s, 3H), 3.80 (m, $^1$H, simplifies to d, J=8.7 Hz, with D$_2$O), 5.01 (m, $^1$H, simplifies to d, J=8.7 Hz, with D$_2$O), 5.68 (d, J=6.0 Hz, $^1$H, exchanges with D$_2$O), 6.59 (d, J 5.7 Hz, $^1$H), 7.31 (d, J=5.7 Hz, $^1$H), 7.88 (d, T=8.3 Hz, 2H), 8.11 (d, J=8.3 Hz, 2H) and 9.05 (d, J=8.4 Hz, $^1$H exchanges with D$_2$O).

Anal. Calcd. for C$_{17}$H$_{16}$F$_3$NO$_3$S: C, 54.98; H, 4.34; N, 3.77.

Found: C, 55.01; H, 4.28; N, 3.70.

EXAMPLE 17

5,6-Dihydro-6-hydroxy-2-nitro-7-(4-trifluoromethylbenzamido) -7H-thieno]3,2-b]pyran The title compound was prepared as described in Example 9 starting with 5,6-dihydro-6-hydroxy-7-(4-trifluoromethylbenzamido) -7H-thieno[3,2-b]pyran (1.5 g, 4.04 mmol) and 90% nitric acid (2.5 mL) in acetic acid (20 mL) to give a yellow solid, 0.165 g (10%): mp 219°-220° C.; IR (KBr): 3310, 1661, 1538 and 1504 cm$^{-1}$; MS: m/z 417 (MH+); $^1$$^1$H NMR (DMSO-d$_6$): w 1.26 (s, 3H), 1.45 (s, 3H), 3.92 (m, $^1$H, simplifies to d, J=8.9 Hz, with D$_2$O), 4.98 (m, $^1$H, simplifies to d, J=8.9 Hz, with D$_2$O), 5.99 (d, $^1$H, exchanges with D 20), 7.74 (s, $^1$H), 7.92 (d, J=8.5 Hz, 2H), 8.12 (d, J=8.5 Hz, 2H) and 9.30 (d, $^1$H, exchanges with D$_2$O).

Anal. Calcd. for $C_{17}H_{15}F_3N_2O_5S$: C, 49.03; H, 3.63; N. 6.73

Found: C, 49.01; H, 3,27; N, 6.60.

EXAMPLE 18

5,6-Dihydro-6-hydroxy-5,5-dimethyl-7-pyrrolidin-1-yl-7H-thieno [3,2--b]pyran

Sodium hydride (60% in mineral oil, 0.145 g, 3.64 mmol) was added to a solution of 6-bromo-5,6-dihydro-7-hydroxy-7H-thieno [3,2-b]pyran (0.87 g, 3.31 mmol) in N,N-dimethylformamide (30 mL) at 5° C. The resultant solution was stirred at rt for 1.5 h. Pyrrolidine (0.91 mL, 10.9 mmol) was added to the solution and stirred at rt for 17 h. The solution was poured into ice water, and the product was extracted into diethyl ether, washed several times with water and saturated aqueous sodium chloride, and dried over magnesium sulfate. The solvent was evaporated in vacuo and the residue was purified by flash chromatography using 5% methanol in dichloromethane as the eluant to give the product, 0.55 g (66%), as a yellow solid: mp 85°–89° C.; IR (KBr): 3540, 2970, 2965, 1551 and 1394 cm$^{-1}$; MS: m/z 254 (MH+); $^{11}$H NMR (CDCl$_3$): w 1.22 (s, 3H), 1.50 (s, 3H), 1.83 (m, 4H), 2.85 (m, 4H), 3,27 (bs, $^1$H, exchanges with D 0), 3.62 (d, J=9.3 Hz, 1H), 3.90 (d, J=9.3 Hz, $^1$H), 6.59 (d, J=5.4 Hz, $^1$H) and 7.03 (d, J=5.4 Hz, $^1$H).

Anal. Calcd. for $C_{13}H_{19}NO_2S$: C, 61.63; H, 7.56; N, 5,53; S, 12.66.

Found: C, 61.38; H, 7.60; N, 5.48; S, 12.58.

EXAMPLE 19

6-Hydroxy-5,5-dimethyl-7-(2-oxohexamethyleneimin-1-yl)-7H-thieno [3,2-b]pyran

The title compound was prepared as described for Example 3 starting with the bromoalcohol (2.5 g, 9.5 mmol) and caprolactam (2.1 g, 19.0 mmol) to give 1.35 g (48%): mp 153°–154° C.; IR (KBr): 3200, 1615, 1523 cm$^{-1}$; MS: m/z 296 (MH+); $^{11}$H NMR (CDCl$_3$) δ 7.13 (d, J=5.4 Hz, $^1$H), 6.58 (d, J=5.4 Hz, $^1$H), 5.75 (d, J=9.2 Hz, $^1$H), 3.69 (m, 1H), 3.36 (d, J=4.9 Hz, $^1$H), 3,23 (m, 2H), 2.64 (m, 2H), 1.86 (m, 6H), 1.47 (s, 3H), 1.29 (s, 3H).

Anal. Calcd. for $C_{15}H_{21}NO_3S$: C, 60.99; H, 7.17; N, 4.74; S, 10.85.

Found: C, 60.76; H, 6.93; N, 4.76; S. 10.66.

EXAMPLE 20

6-Hydroxy-5,5-dimethyl-2-nitro-7-(2-oxobexamethyleneimin-1-yl) thieno]3,2-b]pyran The title compound was prepared as described for Example 5 starting with 6-hydroxy-5,5-dimethyl-7-(2-oxohexamethyleneimin-1-yl) thieno[3,2-b]pyran (0.5 g, 1.7 mmol) and nitric acid (90%, 0.55 mL, 12.3 mol) in acetic acid (15 ML) to give 410 mg (71%): mp 218°–219° C.; IR (KBr): 3340, 1627, 1503 cm$^{-1}$; MS: m/z 341 (MH+) ; $^1$H NMR (CDCl$_3$) δ 7.40 (s, $^1$H), 5.80 (bd, $^1$H), 3.73 (d, J=9.5 Hz, $^1$H), 3,28 (m, 4 H), 2.66 (m, 2 H), 1.87 (m, 4 H), 1.50 (s, 3H), 1.32 (s, 3H).

Anal. Calcd. for $C_{15}H_{20}N_2O_5S$: C, 52.93; H, 5.92; N, 8.23.

Found: C, 52.71; H, 5.74; N, 7.84.

EXAMPLE 21

6-Acetoxy-5,5-dimethyl-7-(2-oxohexamethyleneimin-1-yl)-thieno -[3,2-b]pyran

The title compound was prepared as described for Example 8 starting with 6-hydroxy-5,5-dimethyl-7-(2-oxohexamethyleneiminyl) thieno[3,2-b]pyran (1.5 g, 5.1 mmol) and 70% perchloric acid (10 drops) in acetic anhydride (15 mL) to give 1.5 g (87%): mp 153°–154° C.; IR (KBr): 1668, 1615, 1563 cm$^{-1}$; MS: m/z 338 (MH+) ; $^1$H NMR (CDCl$_3$) δ 7.11 (d, J=5.3 Hz, $^1$H), 6.57 (d, J=5.3 Hz, $^1$H), 5.99 (d, J=9.0 Hz, $^1$H), 5.10 (d, J=9.0 Hz, $^1$H), 3.16 (m, 2H), 2.52 (m, 2H), 2.09 (s, 3H), 1.66 (m, 6H), 1.36 (s, 3H), 1.34 (s, 3H).

Anal. Calcd. for $C_{17}H_{23}NO_4S$: C, 60.51; H, 6.87; N, 4.15.

Found: C, 60.71; H, 6.54; N, 3.76.

EXAMPLE 22

6-Hydroxy-5,5-dimethyl-7-(2-5-dioxol)iverazin-1-yl)-7H-thieno [3,2-b]pyran

The title compound was prepared as described for Example 3 starting with the bromoalcohol (2.5 g, 9.5 mmol) and glycine anhydride (2.2 g, 19.0 mmol) to give 0.58 g (36%); mp 132°–133° C.; IR (KBr): 3210, 1627, 1510 cm$^{-1}$; MS: 297 (MH+). $^1$H NMR (CDCl$_3$) δ 7.13 (d, J=5.4 Hz, $^1$H), 6.58 (d, J=5.4 Hz, $^1$H), 5.77 (d, J=9.2 Hz, $^1$H), 3.54 (m, 1H), 3.46 (d, J=4.9 Hz, $^1$H), 3,23 (s, 2H), 2.79 (s, 2H), 1.48 (s, 3H), 1.31 (s, 3H).

Anal. Calcd. for $C_{13}H_{16}N_2O_4S$: C, 52.69; H, 5.44; N, 9.45.

Found: C, 52.53; H, 5.23; N, 9.67.

EXAMPLE 23

5,6-Dihydro-6-hydroxy-5,5-dimethyl-7-Diveridin-1-yl-7H-thieno [3,2-b]pyvran

The title compound was prepared as described in Example 18 starting with 6-bromo-5,6-dihydro-7-hydroxy-5,5-dimethyl-7H-thieno [3,2-b]pyran (1.5 g, 5.7 mmol) and piperidine (1.7 mL, 17.1 mmol) in N,N-dimethylformamide (25 ML) to give an off white solid, 0.977 (64%): mp 68°-70 0C.; IR (KBr): 2937, 1549 and 1396 cm$^{-1}$; MS: m/z 162 (MH+); $^{11}$H NMR (CDCl$_3$) δ 1.20 (s, 3H), 1.50 (s, 3H), 1.52 (m, 2H), 1.61 (m, 4H), 2.65 (m, 2H), 2.78 (m, 2H), 3,20 (bs, 1H, exchanges with D$_2$O), 3.55 (d, J=9.3 Hz, $^1$H), 3.68 (d, J=9.3 Hz, $^1$H), 6.58 (d, J=5.4 Hz, $^1$H) and 7.04 (d, J=5.4 Hz, $^1$H).

Anal. calcd. for $C_{14}H_{21}NO_2S$: C, 62.89; H, 7.92; N, 5.23; S, 11.99.

Found: C, 62.86; H, 8.10; N, 5.23; S, 12.12.

EXAMPLE 24

6-Benzoyloxy-5,6-dihydro-5,5-dimethyl-7-(2-oxopyrrolidin-1-yl) -7H-thieno]3,2-b]pyran A mixture of 5,6-dihydro-6-hydroxy-5,5-dimethyl-7-(2-oxopyrrolidin-1-yl) -7H-thieno[3,2-b]pyran (1.0 g, 3.74 mmol), benzoic anhydride (10 g) and 70% perchloric acid (10 drops) were heated to 80° C. for 2 h. The mixture was poured into ice water and extracted with dichloromethane and purified by flash chromatography using 1% methanol in dichloromethane as the eluant. The product was further purified by medium pressure chromatography using the same eluant, to give the product, 0.893 g (64%), as a grey solid: mp 130°–1320° C.; IR (KBr): 2981, 1721, 1695 and 1561 cm$^{-1}$; MS: m/z 372 (MH+); $^{11}$H NMR (CDCl$_3$) δ 1.43 (s, 3H), 1.49 (s, 3H), 1.96 (m, 2H), 2.23 (m, $^1$H), 2.33 (m, $^1$H), 3.31 (m, $^1$H), 3.47 (m, $^1$H), 5.44 (d, J=9.3 Hz, 1H), 5,64 (d, J=9.3 Hz, $^1$H), 6.62 (d, J=5.3 Hz, $^1$H), 7.15 (d, J=5.3 Hz, $^1$H), 7.46 (t, J=7.4 Hz, 2H), 7.59 (t, J=7.4 Hz, $^1$H) and 8.03 (d, J=7.4 Hz, 2H).

Anal. calcd. for $C_{20}H_{21}NO_4S$: C, 64.67; H, 5.70; N, 3.77; S, 8.63.
Found: C, 64.94; H, 5,57; N, 3.59; S, 8.64.

EXAMPLE 25

6-Hydroxy-5,5-dimethyl-7-(nicotinamido)-7H-thieno[3,2-b]pyran

The title compound was prepared as described for Example 3 starting with 6-bromo-5,6-dihydro-7-hydroxy-5,5-dimethyl-7H -thieno[3,2-b]pyran (4.0 g, 15.2 mmol) and nicotinamide (3.7 g, 30.4 mmol) to give 1.1 g (24%): m.p. 248°–49° C.; IR (KBr): 3329, 3312,1648, 1594, 1569 cm$^{-1}$; MS: m/z 305 (MH+); $^{1}$H NMR (CDCl$_3$) δ 9.02 (s, $^{1}$H), 8.79 (d, J=5,6 Hz, $^{1}$H), 8.14 (d, J=5,6 Hz, $^{1}$H), 7.44 (m, $^{1}$H), 7.18 (d, J=5.4 Hz, $^{1}$H), 6.64 (d, J=5.4 Hz, $^{1}$H), 6.55 (d, J=5,6, 1H), 5.20 (m, $^{1}$H), 4.46 (brs, $^{1}$H), 3.81 (d, J=9.4 Hz, 1H), 1.50 (s, 3H), 1.36 (s, 3H).

Anal. Calcd. for $C_{15}H_{16}N_2O_3S$: C, 59.19; H, 5.30; N, 9.20.
Found: C, 58.91; H, 5.10; N, 9.13.

EXAMPLE 26

6-Hydroxy-7-(2-imidazolidon-1-yl)-5,5-dimethyl-7H-thieno [3,2-b]pyran

The title compound was prepared as described for Example 3 starting with 6-bromo-5,6-dihydro-7-hydroxy-5,5-dimethyl-7H-thieno [3,2-b]pyran (4.0 g, 15.2 mmol) and 2-imidazolidone (2.9 g, 30.4 mmol) to give 630 mg (15%): m.p. 156°–58° C.; IR (KBr): 3390, 1698, 1565, 1489 cm$^{-1}$; MS: m/z 309 (MH+); $^{1}$H NMR (CDCl$_3$)δ 7.13 (d, J=5.4 Hz, 1H), 6.54 (d, J=5.4 Hz, 1H), 5.15 (m, 1H), 4.67 (m, 2H), 3.79 (d, J=9.4 Hz, 1H), 3.24 (m, 2H), 1.48 (s, 3H), 1.31 (s, 3H).

Anal. Calcd. for $C_{12}H_{16}N_2O_3S$: C, 53.71; H, 6.01; N, 10.44.
Found: C, 53.78; H, 6.14; N, 10.42.

EXAMPLE 27

6-Hydroxy-5,5-dimethyl-7-(isonicotinamido)-7H-thieno [3,2-b]-pyran

The title compound was prepared as described for Example 3 starting with 6-bromo-5,6-dihydro-7-hydroxy-5,5-dimethyl-7H-thieno [3,2-b]pyran (4.0 g, 15.2 mmol) and isonicotinamide (3.7 g, 30.4 mmol) to give 510 mg (11%): m.p. 223°–34° C.; IR (KBr): 3324, 3304,1649, 1569, 1536 cm$^{-1}$; MS: m/z 305 (MH+); 1H NMR CDCl$_3$) δ 8.78 (d, J=5.8 Hz, 2H), 7.63 (d, J=5.8 Hz, 2H), 7.18 (d, J=5.4 Hz, 1H), 6.63 (d, J=5.4 Hz, 1H), 5.19 (m, 1H), 4.28 (brs, 1H), 3.79 (d, J=9.4 Hz, 1H), 1.49 (s, 3H), 1.35 (s, 3H).

Anal. calcd. for $C_{15}H_{16}N_2O_3S$: C, 59.19; H, 5.30; N, 9.20.
Found: C, 58.85; H, 5.07; N, 9.05.

EXAMPLE 28

5,6-Dihydro-5,5-dimethyl-7-(pyrrolidin-1-yl)-7H-thieno[3,2-b]-pyran

A solution of 5,6-dihydro-5,5-dimethylthieno[3,2-b]pyran-7-one (1.0 g, 5,5 mmol), pyrrolidine (2.3 ml, 27.4 mmol) sodium cyanoborohydride (0.345 g, 5,5 mmol) and 1N aqueous hydrochloric acid (5,5 ml, 5,5 mmol) in methanol (15 ml)-was stirred at rt for 1 day. Additional sodium cyanoborohydride (0.345 g, 5,5 mmol) was added and the solution was stirred an additional 1 day; additional sodium cyanoborohydride (1.0 g, 15.9 mmol) was added again and the mixture stirred 5 additional days. The mixture was poured into water (100 ml) and extracted with dichloromethane. The dichloromethane solution was washed with water and dried over sodium sulfate. The solvent was evaporated in vacuo and the residue was purified by medium pressure chromatography using 2% methanol in dichloromethane as the eluant to give the product 0.70 g (54%) as a yellow solid; mp 49°–50° C.; IR(KBr): 2971, 1560 and 1394 cm$^{-1}$; MS:m/z 238 (MH+); H NMR-(CDCl$_3$): δ 1.27(s,3H), 1.45(s3H), 1.80(m,4H), 1.91(m,2H), 2.76(m,4H), 4.09(m,1H), 6.57(d,J=5.4 Hz,1H), and 7.04(d,J=5.4 Hz,1H).

Anal. Calcd. for $C_{13}H_{19}$ NOS:C,65.78; H,8.07; N,5.90.
Found: C,65.35; H,8.24; N,5.97.

EXAMPLE 29

7-(4-Cyanobenzamido)-5,6-dihydro-6-hydroxy-5,5-dimethyl-7H-thieno [3,2-b]pyran The title compound was prepared as described in Example 3 starting with 6-bromo-7-hydroxy-5-6-dihydro-5,5-dimethyl-7H-thieno [3,2-b]pyran (6.73 g, 25.6 mmol), sodium hydride (2.14 g, 53.8 mmol), 4-cyanobenzamide (12.0 g, 82.1 mmol) and N,N-dimethylformamide (75 ml) to give the product, after recrystallization from dichloromethane and hexanes, 0.82 g (10%) as a colorless solid; mp 177°–178° C.; 1R(KBr): 3420, 1648, 1545 and 1496 cm$^{-1}$; MS: m/z 329 (MH+); $^{1}$H NMR (CDCl$_3$) δ 1.35 (s,3H),1.50 (s,3H), 3.79 (dd,J=7.8 Hz, J=2.5Hz, 1H, simplifies to d, J-7.8Hz with D$_2$O), 4.31 (d,J=2.5Hz, 1H, exchanges with D$_2$O), 5.17 (m, 1H), 6.56(bd, J=6.8Hz, 1H), 6.63(d,J=5.4 Hz,1H), 7.18(d,J=5.4 Hz, 1H), 7.78 (d,J=8.2 Hz, 2H) and 7.91 (d, J=8.2 Hz,2H).

Anal. Calcd for $C_{17}H_{16}N_2O_3S$: C,62.18; H,4.91; N,8.53; S,9.75.
Found: C,62.10; H, 4.74; N, 8.21; S,9.56.

EXAMPLE 30

6-Acetoxy-2-acetyl-7-(4-trifluoromethylbenzamido)-5,6-dihydro-5,5-dimethyl -7H-thieno[3,2b]pyran The title compound was prepared as described in Example 6 starting with 7-(4-trifluoromethylbenzamido)-5,6-dihydro -6-hydroxy-5,5-dimethyl-7H-thieno[3,2-b]pyran (1.5 g, 4.04 mmol), perchloric acid (70%, 10 drops) and acetic anhydride (20 ml) to give the product after crystallization from dichloromethane and hexanes 0.382 g (21%) as a colorless solid; mp 225°–227° C.; IR (KBr):1755, 1668, 1654, 1541 and 1471 cm$^{-1}$; MS=m/z 456 MH+); $^{1}$H NMR (CDCl$_3$): w 1.41(s,3H), 1.43 (s,3H), 2.13 (s,3H), 2.47 (s,3H), 5.17 (d,J=9.3 Hz,1H), 5.42(m,1H), 6.77 (bd,J=7.9Hz,1H), 7.14 (s,1H), 7.72 (d,J=8.3 Hz, 2H) and 7.88 (d,J=8.3 Hz,2H).

Anal. calcd. for $C_{21}H_{20}F_3NO_5S$: C,55.42; H,4.43; N,3.08.
Found: C,55.06; H, 4.28; N,2.82.

EXAMPLE 31

2-Acetyl-7-(4-trifluoromethylbenzamido)-5,6-dihydro-6-hydroxy -5,5-dimethyl-7H-thieno[3,2-b]pyran A mixture of potassium carbonate (92 mg, 0.67 mmol) and 6-acetoxy -2-acetyl-7-(4-trifluoromethylbenzamido)-5,6-dihydro-5,5-dimethyl-7H-thieno[3,2-b]pyran (0.30 g, 0.66 mmol) in methanol was stirred at rt for 3h. The mixture was poured into ice water and a white solid crystallized within ten minutes. The solid was collected by filtration, washed with water, air dried and recrystallized from dichloromethane and hexanes to give the product 0.21 g (77%) as a colorless solid; mp 227°-229° C.; IR (KBr): 1652, 1541 and 1414 cm$^{-1}$; MS: m/z 414 MH+);$^1$H NMR (CDCl$_3$) δ 1.36 4.37(bs,1H exchanges with D$_2$O), 5.24 (m,1H), 6.61(bd,1H), 7.17(s,1H), 7.74 (d,J=8.2Hz,2H) and 7.94 (d,J=8.2Hz,2H).

Anal. calcd. for c$_{19}$ H$_{18}$F$_3$NO$_4$S: C,55.20; H,4.40; N,3.39.

Found: C, 55.21; H,4.21; N, 3.29.

EXAMPLE 32

5,6-Dihydro-6-methoxy-5,5-dimethyl-7-(2-oxopyrrolidin--1-yl) 7H-thieno[3,2-b]pyran 5,6-Dihydro-6-hydroxy-5,5-dimethyl-7-(2-oxopyrrolidin-1-yl) -7H-thieno[3,2-b]pyran (1.1 g, 4.11 mmol) was added to a mixture of sodium hydride (60% in mineral oil, 0.172 g, 4.32 mmol) in N,N-dimethylformamide (20 ml) at 0° C. and stirred for 1.5h. Methyl iodide (0.28 ml, 4.52 mmol) was added to the resultant mixture and the mixture stirred at rt for 1h. The mixture was poured into ice water (100 ml) and extracted with dichloromethane. The dichloromethane solution was washed with water (5x) and dried over magnesium sulfate. The solvent was evaporated in vacuo and the residue was crystallized from dichloromethane and hexanes to give the product 0.825 g (71%) as a colorless solid; mp 117°-118° C.; IR(KBr): 2979, 1677, 1572 and 1420 cm$^{-1}$; MS: m/z 282 (MH+); $^1$H NMR (CDCl$_3$) δ 1.27 (s,3H), 1.48(s,3H), 2.05(m,2H), 2.50(m,2H), 3.33(m,2H), 3.41(d,J=8.8Hz, 1H), 3.51(s,3H), 5.33(d,J=8.8Hz, 1H), 6.55(d,J=5.4Hz, 1H) and 7.09 (d,J=5.4Hz, 1H).

Anal Calcd. for C$_{14}$H$_{19}$NO$_3$: C,59.76; H,6.81; N,4.98.

Found: C,59.73; H,6.46; N,4.81.

EXAMPLE 33

7-Azido-5,6-dihydro-6-hydroxy-5,5-dimethyl-7H-thieno [3,2-b]-pyran.

Sodium Hydride (60% in oil, 3.77 g, 94.1 mmol) was added to a solution of 6-bromo-7-hydroxy-5,6-dihydro-5,5-dimethyl-7H-thieno [3,2-b]pyran (23.6 g, 89.7 mmol) in N,N-dimethyl formamide (275 ml) at 0° C. The mixture was stirred at rt for 1.5h and sodium azide (17.0 g, 0.269 mol) was added. The resultant mixture was stirred at rt for 3 days, then poured into ice water (1200 ml) and extracted with diethyl ether. The ether solution was washed with water (5x) and dried over magnesium sulfate. The solvent was evaporated in vacuo and the residue was purified by flash chromatography using 15% hexanes in dichloromethane as the eluant to give the product 5.1 g (25%) as a tan solid; mp 48°-50° C.; IR (KBr): 3471, 2104, 1568 and 1402 cm$^{-1}$; MS:m/z 226(MH+); $^1$H NMR (CDCl$_3$) δ1.31 (s,3H), 1.47 (s,3H), 2.29 (d,J=5.BHz, $^1$H, exchanges with D$_2$O), 3.78(m,1H, simplifies to d, J=7.0 Hz, with D$_2$O), 4.44(d,J=7.0 Hz, $^1$H), 6.58 (d,J=5.4Hz,1H) and 7.18 (d,J=5.4 Hz,1H).

Anal. Calcd. for C$_9$H$_{11}$N$_3$O$_2$S: C, 47.99; H,4.92; N,18.65.

Found: C,48.36; H,4.91; N,18.12.

EXAMPLE 34

7-Amino-5,6-dihydro-6-hydroxy-5,5-dimethyl-7H-thieno]3,2-b]-pyran

7-Azido-5,6-dihydro-6-hydroxy-5,5-dimethyl-7H-thieno[3,2-b]pyran (2.0 g, 8.88 mmol) was added carefully in small portions to a mixture of lithium aluminum hydride (0.67 g, 17.8 mmol) in diethyl ether (40 ml). The resultant mixture was stirred an additional 1h at rt and quenched with successive dropwise addition of water (0.7 ml), 15% aqueous sodium hydroxide (0.7 ml) and water (2.0 ml). The aluminum salts were removed by filtration and the ether solution was dried over magnesium sulfate. The solvent was evaporated in vacuo to give the product 1.64 g (93%) as a beige solid; mp 111°-116° C.; IR(KBr):3110, 2971, 1565 and 1403cm$^{-1}$; MS:m/z 200 (MH+); $^1$H NMR (CDCl$_3$): δ 1.24(s,3H), 1.48(s,3H), 1.85(bs,3H, exchanges with D$_2$O), 3.38 (d,J=8.6 Hz,1H), 3.70 (d,J=8.6 Hz,1H), 6.55 (d,J=5.4Hz,1H) and 7.07(d,J=5.4Hz,1H).

Anal. Calcd. for C$_9$H$_{13}$NO$_2$S: C,54.25; H,6.58; N,7.03; S,1609.

Found: C,54.80; H,6.23; N,6.44; S,15.91.

EXAMPLE 35

7-(4-Fluorobenzamido)-5,6-dihydro-6-hydroxy-5,5-dimethyl -7H-thienor3,2-b]pyran

A solution of 4-fluorobenzoyl chloride (0.91 ml, 7.72 mmol) in dichloromethane (5 ml) was slowly added to a solution of 7-amino-5,6-dihydro-6-hydroxy-5,5-dimethyl-7H-thieno [3,2-b]pyran (1.4 g, 7.03 mmol) and triethylamine (2.9 ml, 21.1 mmol) in dichloromethane (30 ml) at 0° C. The resultant mixture was stirred an additional 1h at 0° C., then washed with 1N hydrochloric acid, then with saturated aqueous sodium bicarbonate and dried over magnesium sulfate. The solvent was evaporated in vacuo and the residue was recrystallized from dichloromethane and hexanes to give the product 1.919 (85%) as a colorless solid; mp 162°-164° C.; IR (KBr): 3365, 1648, 1604, 1535 and 1500 cm$^{-1}$; MS:m/z 322 (MH+); $^1$H NMR (CDCl$_3$): δ 1.35(s,3H), 1.50(s,3H), 3.76(dd, J=2.OHz, J=7.9Hz, $^1$H, simplifies to d,J=7.9Hz, with D$_2$O), 4,72(d, J=2.OHz, $^1$H, exchanges with D$_2$O), 5.14 (m,1H), 6.45(bd,1H), 6.62 (d,J=5.4Hz, $^1$H), 7.15 (m,3H), and 7.82 (m,2H).

Anal Calcd. for C$_{16}$H$_{16}$ FNO$_3$S: C, 59.80; H,5.02, N,4.35.

Found: C,59.81; H,5.07; N,4.18.

EXAMPLE 36

7-Benzamida-5,6-dihydro-6-hydroxy-5,5-dimethyl-7H-thieno-[3,2-b]pyran

The title compound was prepared as described in Example 34 starting with benzoyl chloride (0.95 ml), triethylamine (3.3 ml, 23 mmol) and 7-amino-5,6-dihydro-6-hydroxy-5, 5-dimethyl-7H-thieno[3,2-b]pyran (1.55 g, 7.78 mmol) in dichloromethane (35 ml) to give the product 1.07 g (45%) as a colorless solid; mp 219°-220° C.;IR(KBr):3398, 1657, 1526 and 1490 cm$^{-1}$; MS:m/z 304 (MH +); $^1$H NMR (DMSO-d$_6$):w1.21 (5,3H), 1.39 (5,3H), 3.81 (m,1H, simplifies to d, J=8.8 Hz, with D$_2$O), 5.00 (m,1H simplifies to d, 5=8.8Hz, with D$_2$O), 5.61(d,J=6.OHz, $^1$H, exchanges with D$_2$O), 6.58(d,J=5.3Hz,1H), 7.29(d,J=5.3Hz,1H), 7.47(m,3H), 7.92(dd,J=1.3Hz, J=8.2Hz,2H) and 8.79 (d,J=8.3Hz, $^1$H, exchanges with D$_2$O).

Anal. Calcd. for $C_{16}H_{17}NO_3S$: C,63.35; H,5.65; N,4.62; S,10.57.

Found: C,63.12; H,5.28; N,4.24; S,10.37.

In a similar manner, the following compounds were prepared according to the method described in Example 35 where $R_1=H$, $R_5=H$, and $R_7,R_8=CH_3$.

| Ex. | $NR_3R_4$ | $R_6$ | $R_2$ | m.p.(°C.) |
|---|---|---|---|---|
| 37 | m-ClPhCONH | OH | H | 165-167 |
| 38 | m-FPhCONH | OH | H | 225(dec) |
| 39 | p-MeOPhCONH | OH | H | 218-219 |
| 40 | p-MePhCONH | OH | H | 226-227 |
| 41 | m,p-F$_2$PhCONH | OH | H | 176-181 |
| 42 | o,p-F$_2$PhCONH | OH | H | 110-113 |
| 43 | p-FPhSO$_2$NH | OH | H | 156-157 |
| 44 | 2-furoylNH | OH | H | 132-134 |
| 45 | 2-thenoylNH | OH | H | 234-236 |
| 46 | cinnamoylNH | OH | H | 188-189 |
| 47 | F$_5$-PhCONH | OH | H | 215-217 |
| 48 | o-FPhCONH | OH | H | 172-174 |
| 49 | acetamido | OH | H | 172-174 |
| 50 | CF$_3$CONH | OH | H | 160-161 |

EXAMPLE 51 trans-5,6-Dihydro-6-hydroxy-7-(2-isoindolon-1-yl)-5,5-dimethyl-7H-thieno[3,2-b]pyran A solution of 7-amino-5,6-dihydro-6-hydroxy-5,5-dimethyl-7H-thieno[3,2-b]pyran (1.3 g, 6.5 mmol) in MEOH (5 mL) was slowly added to solution of 2-carbomethoxybenzaldehyde (5.4 g, 32.7 mmol) in 20 ML MeOH followed by catalytic zinc chloride. The mixture was stirred at rt for 2 h. Sodium cyanoborohydride (0.75 g, 12.2 mmol) was added and the mixture was heated to 40° C. overnight. The reaction was poured into ice water and extracted twice with dichloromethane. After concentration in vacuo, the oil was dissolved in 20 mL toluene and heated to 100° C. for 5h. The mixture was concentrated and the resulting oil was purified by chromatography (flash, 9:1 dichloromethane-acetone) to give 1.8 g (88%) of the title compound: mp 211°-212° C.; MS:m/z 316MH+); $^1$H NMR (CDCl$_3$): δ 1.21 (s, 3H), 1.57 (s, 3H), 3.99 (d,d, J=3.1 Hz, $^1$H), 4.46 (d, J=6.0 Hz, $^1$H), 5,56 (d, J=9.2Hz, 1H), 6.60 (d, J=5.4 Hz,1H), 7.09 (d, J=5.4 Hz,1H), 7.23-7.64 (m, 4H).

Anal Calcd. for $C_{17}H_{17}NO_3S$: C,64.74; H,5.43; N,4.44.

Found: C,64.89; H, 5.53; N,4.42.

In a similar manner, the following compounds were prepared by the method described in Example 5 where $R_1=H$, $R_5=H$, and $R_7$, $R_8=CH_3$.

| EX | $NR_3R_4$ | $R_6$ | $R_2$ | m.p.(°C.) |
|---|---|---|---|---|
| 52 | 3-pyridylCONH | OH | 2-NO$_2$ | 212-213 |
| 53 | m-ClPhCONH | OH | 2-NO$_2$ | 109-111 |
| 54 | p-FPhCONH | OH | 2-NO$_2$ | 198-202 |
| 55 | p-MeOPhCONH | OH | 2-NO$_2$ | 197-198 |
| 56 | m-FPhCONH | OH | 2-NO$_2$ | 178-179 |
| 57 | p-MePhCONH | OH | 2-NO$_2$ | 107-109 |
| 58 | m,p-F$_2$PhCONH | OH | 2-NO$_2$ | 179-181 |
| 59 | 2-thenoylNH | OH | 2-NO$_2$ | 196-198 |
| 60 | 2-furoylNH | OH | 2-NO$_2$ | 195-197 |
| 61 | o-FPhCONH | OH | 2-NO$_2$ | 98-100 |
| 62 | F$_5$-PhCONH | OH | 2-NO$_2$ | 150-152 |
| 63 | cinnamoylNH | OH | 2-NO$_2$ | 118-120 |
| 64 | acetamido | OH | 2-NO$_2$ | 220-224 |
| 65 | 2-oxopyridin-1-yl | OH | 2-NO$_2$ | 113-114 |
| 66 | 2-isoindolone | OH | 2-NO$_2$ | 134-136 |

In a similar manner, the following compounds were prepared by the method described in Examples 6&& where $R_1=H$, $R_5=H$, and $R_7,R_8=CH_3$.

| EX | $NR_3R_4$ | $R_6$ | $R_2$ | m.p.(°C.) |
|---|---|---|---|---|
| 67 | 3-pyridylCONH | OAc | 2-Ac | 257-258 |
| 68 | PhCONH | OAc | 2-Ac | 251-253 |
| 69 | p-FPhCONH | OH | 2-Ac | 191-193 |
| 70 | PhCONH | OH | 2-Ac | 210-216 |
| 71 | m-ClPhCONH | OH | 2-Ac | 132-133 |
| 72 | m,p-F$_2$PhCONH | OH | 2-Ac | 225-227 |
| 73 | p-ClPhCONH | OAc | 2-Ac | 210-212 |
| 74 | p-ClPhCONH | OH | 2-Ac | 212-214 |
| 75 | p-MeOPhCONH | OH | 2-Ac | 156-157 |
| 76 | o,p-F$_2$PhCONH | OH | 2-Ac | 168-170 |
| 77 | o-FPhCONH | OH | 2-Ac | 210-212 |
| 78 | m-NO$_2$PhCONH | OH | 2-Ac | 205-206 |
| 79 | p-MePhCONH | OH | 2-Ac | 158-160 |
| 80 | isonicatinamido | OAc | 2-Ac | 138-139 |
| 81 | pyrrolidinon-1-yl | OMe | 2-Ac | 174-175 |
| 82 | pyrrolidinon-1-yl | OH | 2-CF$_3$CO | 111-113 |
| 83 | acetamido | OH | 2-Ac | 165-168 |
| 84 | piperidon-1-yl | OH | 2-Ac | 124-126 |
| 85 | 2-isoindolone | OH | 2-Ac | 198-201 |

In a similar manner, the following compounds were prepared by the method described in Example 4 where $R_1=H$, $R_5=H$, and $R_7,R_8=CH_3$.

| EX | $NR_3R_4$ | $R_6$ | $R_2$ | m.p.(°C.) |
|---|---|---|---|---|
| 86 | p-FPhCONH | OH | 2-Br | 157-159 |
| 87 | p-ClPhCONH | OH | 2-Br | 167-169 |
| 88 | p-FPhSO$_2$NH | OH | 2-Br | 85-86 |
| 89 | pyrrolidinon-1-yl | OAc | 2-Br | 130-131 |
| 90 | piperidon-1-yl | OMe | 2-Br | 171-172 |

EXAMPLE 91 trans-2-Carbomethoxy-5,6-dihydro-6-hydroxy-5,5-dimethyl-7-(2-oxopiperidin-1-yl)-7H-thieno[3,2-b]pyran A solution of trans-2-bromo-5,6-dihydro-6-hydroxy-5,5-dimethyl -7-(2-oxopiperidin-1-yl)-7H-thieno[3,2-b]pyran (1.35 g, 3.75 mmol), triethylamine (0.87 mL, 6.25 mmol) and bis(triphenylphosphine)-palladium(II) chloride (80 mg, 0.11 mmol) in methanol (120 mL) was heated in a stainless steel Parr pressure reactor pressurized with carbon monoxide (160 psi) at 100° C. for four days. The resultant solution was poured into water and extracted with dichloromethane. The organic phase was dried over magnesium sulfate and the solvent was evaporated in vacuo. The product was purified by flash chromatography using 2% methanol in dichloromethane as the eluant to give the product, 0.83 g (65%) as a colorless solid: mp 104°-106° C.; IR(KBr): 1718, 1618 and 1565 cm$^{-1}$; MS: m/z 340MH+); $^1$H NMR(CDCl$_3$): δ 1.29 (s, 3H), 1.49 (s, 3H), 1.43 (m, 4H), 2.53 (m, 2H), 3.14 (m, $^1$H), 3.23 (m, 1H), 3.52 (d, J=5.4 Hz, $^1$H, exchanges with D$_2$O), 3.81 (d,d, J=5.4 Hz, J=9.5 Hz, $^1$H, simplifies to d, J=9.5 Hz, with D$_2$O), 3.86 (s, 3H), 5.87 (d, J=9.5 Hz, $^1$H) and 7.24 (s, $^1$H).

Anal. Calcd. for $C_{16}H_{21}NO_5S$: C,56.62; H,6.24; N,4.13; S,9.45

Found: C, 56.60; H, 6.36; N, 4.02; S, 9.30.

EXAMPLE 92 trans-2-Carboxamido-5,6-dihydro-6-hydroxy-5,5-dimethyl-7-(2-oxopiperidin-1-yl)-7H-thienor3,2-b]pyran A solution of trans-2-carbomethoxy-5,6-dihydro-6-hydroxy -5,5-dimethyl-7-(2-oxopiperidin-1-yl)-7H- thieno[3,2-b]pyran (1.0 g, 2.94 mmol) in ammonium hydroxide (10 mL) and methanol (10 mL) was stirred at rt for 5 days. The resultant solution was poured into water (60 mL) and the resultant precipitate was collected by filtration, washed with water and air dried. The product was recrystallized from ethanol to give a colorless solid, 0.58 g (61%): mp 287°–288° C.; IR(KBr): 3200, 1660, 1626, 1615, 1564 and 1480 cm$^{-1}$; MS: m/z 325(MH+); $^1$H NMR(DMSO-d$_6$): w 1.17 (s, 3H), 1.39 (s, 3H), 1.58–1.79 (m, 4H), 2.36 (m, 2H), 2.91 (m, 1H), 3.18 (m, $^1$H), 3.71 (m,1H), 5.60 (bs, 1H), 5.63 (d, J=5.8 Hz, $^1$H, exchanges with D$_2$O), 7.23 (s, $^1$H), 7.39 (bs, $^1$H) and 7.87 (bs, $^1$H).

Anal. Calcd. for $C_{15}H_{20}N_2O_4S$: C,55.54; H,6.21; N,8.64; S,9.88

Found: C, 55.19; H, 6.46; N, 8.63; S, 9.64.

EXAMPLE 93 trans-2-Carboxy-5,6-dihydro-6-hydroxy-5,5-dimethyl-7-(2-oxopiperidin-1-yl) -7H-thienor3,2-b]pyran A solution of trans-2-carbomethoxy-5,6-dihydro-6-hydroxy -5,5-dimethyl-7-(2-oxopiperidin-1-yl)-7H-thieno [3,2-b]pyran (0.60 g, 1.76 mmol) and 1 N aqueous sodium hydroxide (1.9 mL) in methanol (15 mL) was stirred at rt for 18 h. An additional 5 drops of 50% sodium hydroxide was added and the solution stirred for 6 additional hours. The solution was poured into water (100 mL) and acidified with conc. hydrochloric acid. A white precipitate was collected by filtration, washed with water and air dried. The product was triturated in diethyl ether to give a colorless solid, 0.505 g (88%); mp 268°–270° C.; IR(KBr): 1672, 1612, 1582, 1565 and 1490 cm$^{-1}$; MS: m/z 325(MH+); $^1$H NMR(DMSO-D ): w 1.19 (s, 3H), 1.41 (s, 3H), 1.55–1.84 (m, 4H), 2.37 (m, 2H), 2.96 (m, $^1$H), 3.22 (m, $^1$H), 3.38 (bs, $^1$H, exchanges with D$_2$O), 3.75 (d, J=8.8 Hz,1H), 5.60 (bs, $^1$H), 5.69 (bs, $^1$H, exchanges with D$_2$O) and 7.17 (s, $^1$H).

Anal. Calcd. for $C_{15}H_{19}$ NO$_5$S: C,55.37; H,5.89; N,4.30; S,9.85.

Found: C, 55.04; H, 5.95; N, 4.08; S, 9.64.

EXAMPLE 94 trans-6-Benzyloxy-2-bromo-5,6-dihydro-5,5-dimethyl-7-(2-oxopiperidin-1-yl) -7H-thieno[3,2-b]pyran Sodium hydride (60% in mineral oil, 0.47 g, 11.7 mmol) was added to a solution of trans-2-bromo-5,6-dihydro-6-hydroxy-5,5-dimethyl-7-(2-oxopiperidin-1-yl)-7H-thieno-[3,2-b]pyran (4.0 g, 11.1 mmol) in DMF (50 mL) at 0° C. and stirred at rt for 30 min. Benzylbromide (1.45 mL, 12.2 mmol) was added to the resultant solution and stirred at rt for 2 h. The solution was poured into water (200 mL) and extracted into dichloromethane. The organic phase was washed several times with water and dried over magnesium sulfate. The solvent was evaporated in vacuo, and the residue was purified by flash chromatography using 2% methanol in dichloromethane as the eluant. The product was recrystallized from dichloromethane/hexane to give a colorless solid, 3.87 g (77%); mp 146°–147° C.; IR(KBr): 1634 and 1570 cm$^{-1}$; MS: m/z 450 (MH+); $^1$H NMR(CDCl$_3$): 1.32 (s, 3H), 1.50 (s, 3H), 1.53–1.77 (m, 4H), 2.37–2.45 (m, 2H), 2.87 (m, $^1$H), 3.08 (m, $^1$H), 3.69 (d, J=8.6 Hz, $^1$H), 4.60 (d, J=11.8 Hz, $^1$H), 4.73 (d, J=11.8 Hz, $^1$H), 5.90 (bs, $^1$H), 6.54 (s, $^1$H) and 7.26–7.37 (m, 5H).

Anal. Calcd. for $C_{21}H_{24}$ BRNO$_3$S: C,56.00; H,5.37; N,3.11

Found: C, 56.08; H, 5.44; N, 3.04.

EXAMPLE 95 trans-6-Benzyloxy-2-Carbomethoxy-5,6-dihydro-5,5-dimethyl -7-(2-oxopiperidin-1-yl)-7H-thieno[3,2-b]pyran Trans-6-benzyloxy-2-bromo-5,6-dihydro-5,5-dimethyl-7-(2-oxop iperidin-1-yl)-7H-thieno[3,2-b]pyran (1.8 g, 4.0 mmol) was converted to the product using the same procedure described in example 91 to give, after recrystallization from dichloromethane/hexanes a colorless solid, 1.25 g (73%); mp 144°–145° C.; IR(KBr): 1717, 1646, 1569 and 1472 cm$^{-1}$; MS: m/z 430 (MH+); $^1$H NMR(CDCl$_3$): δ 1.32 (s, 3H), 1.53 (s, 3H), 1.61–1.82 (m, 4H), 2.38–2.55 (m, 2H), 2.90 (m, $^1$H), 3.08 (m, 1H), 3.80 (bs, $^1$H), 3.84 (s, 3H), 4.62 (d, J=11.8 Hz, $^1$H), 4.76 (d, J=11.8 Hz, 1H), 6.02 (bs, $^1$H), 7.22 (s, $^1$H) and 7.27–7.38 (m, 5H).

Anal. Calcd. for $C_{23}H_{27}$ NO$_5$S: C,64.31; H,6.34; N,3.26; S,7.46

Found: C, 64.30; H, 6.46; N, 3.21; S, 7.45.

EXAMPLE 96 trans-6-Benzyloxy-2-carboxamido-5,6-dihydro-5,5-dimethyl-7-(2-oxopiperidin-1-yl)-7H-thieno[3,2-b]pyran 1/4 hydrate Trans-6-benzyloxy-2-carbomethoxy-5,6-dihydro-5,5-dimethyl -7-(2-oxopiperidin-1-yl)-7H-thieno[3,2-b]pyran (4.0 g, 9.31 mmol) was converted to the product using the same procedure described in example 92 to give, after trituration in diethyl ether, a colorless solid, 2.69 g (70%); mp 228°–233° C.; IR(KBr): 1667, 1658, 1638, 1613, 1600, 1568 and 1476 cm$^{-1}$; MS: m/z 415 (MH +); $^1$H NMR(DMSO-d$_6$): w 1.21 (s, 3H), 1.49 (s, 3H), 1.49–1.70 (m, 4H), 2.24–2.35 (m, 2H), 2.93–3.00 (m, $^1$H), 3.00–3.25 (m, $^1$H), 3.92 (d, J=9.1 Hz, $^1$H), 4.63 (d, J=11.9 Hz, $^1$H), 4.75 (d, J=11.9 Hz, 1H), 5.76 (bs, $^1$H), 7.26–7.39 (m, 6H), 7.42 (bs, $^1$H) and 7.90 (bs, $^1$H).

Anal. Calcd. for $C_{22}H_{26}N_2O_4S.1/4 H_2O$: C, 63.06; H, 6.37; N, 6.68; S, 7.65.

Found: C, 62.94; H, 6.75; N, 6.61; S, 7.51.

EXAMPLE 97 trans-6-Benzyloxy-2-cyano-5,6-dihydro-5,5-dimethyl-7-(2-oxopiperidin -1-yl)-7H-thieno[3,2-b]pyran Trifluoroacetic anhydride (1.65 mL, 11.7 mmol) in dichloromethane was slowly added to a solution of trans-6-benzyloxy-2-carboxamido-5,6-dihydro-5,5-dimethyl-7-(2-oxopiperidin-1-yl) -7H-thieno[3,2-b]pyran 1/4 hydrate (2.3 g, 5.55 mmol) and pyridine (0.49 mL, 6.10 mmol) in dichloromethane at0° C. and stirred at0° C. for 1 h. The solution was poured into ice water. The organic layer was washed with 1 N hydrochloric acid then 1 N aqueous sodium hydroxide and dried over magnesium sulfate. The solvent was evaporated in vacuo and the residue was purified by flash chromatography using 2% methanol in dichloromethane as the eluant to give a colorless solid which was recrystallized from dichloromethane/hexanes, 1.85 g (84%); mp 174°–178° C.; IR(KBr): 2211, 1653, 1644, 1556 and 1483 cm$^{-1}$; MS: m/z 397 (MH+); $^1$H NMR(CDCl$_3$): δ 1.32 (s, 3H), 1.53 (s, 3H), 1.60–1.84 (m, 4H), 2.34–2.56 (m, 2H), 2.84–3.10 (m, 2H), 3.82 (bs, $^1$H), 4.60 (d, J=11.8

Hz, 1H), 4.76 (d, J=11.8 Hz, 1H), 5.92 (bs, 1H), 7.04 (s, 1H) and 7.29–7.38 (m, 5H).

trans-2-Cyano-5,6-dihydro-6-hydroxy-5,5-dimethyl-7-(2-oxopiperidin-1-yl) -7H-thieno[3,2-b]pyran Boron tribromide (1.0 M in dichloromethane, 17.6 mL, 17.6 mmol) was slowly added to a solution of trans-6-benzyloxy-2-cyano-5,6-dihydro-5,5-dimethyl-7-(2-oxopiperidin-1-yl) -7H-thieno[3,2-b]pyran (1.4 g, 3.5 mmol) in dichloromethane (40 mL) at 0° C. and stirred for 1h. The solution was poured into ice water. The organic layer was washed with water and dried over magnesium sulfate. The solvent was evaporated in vacuo, and the residue was purified by flash chromatography using 3% methanol in dichloromethane as the eluant. The product was recrystallized from dichloromethane/hexanes to give a colorless solid, 0.997 g (93%); mp 212°–214° C.; IR(KBr): 2210, 1624, 1558 and 1486 cm$^{-1}$; MS: m/z 307 (MH+); $^1$H NMR(CDCl$_3$): δ 1.29 (s, 3H), 1.50 (s, 3H), 1.77–1.90 (m, 4H), 2.53 (m, 2H), 3.17 (m, 2H), 3.66 (d, J=5.9 Hz, 1H), 3.80 (dd, J=5.9 Hz, J=9.4 Hz, 1H), 5.85 (d, J=9.4 Hz, 1H), 5.92 (bs, 1H) and 7.07 (s, 1H).

Anal. Calcd. for $C_{15}H_{18}N_2O_3S$: C, 58.80; H, 5.92; N, 9.14; S, 10.47.

Found: C, 58.86; H, 5.83; N, 9.55; S, 10.30.

EXAMPLE 98 trans-5,6-Dihydro-5,5-dimethyl-2-(N,N-dimethylcarboxamido)-7-(2-oxopiperidin-1-yl)-7H-thieno[3,2-b]pyran A solution of trans-2-carbomethoxy-5,6-dihydro-5,5-dimethyl -7-(2-oxopiperidin-1-yl)-7H-thieno[3,2-b]pyran (0.70 g, 2.05 mmol) in dimethylamine (40% aqueous solution, 20 mL) and methanol (20 mL) was stirred at rt for 4 days. The resultant solution was poured into water (200 mL) and extracted with 5% isopropanol in dichloromethane. The organic phase was washed with water and dried over magnesium sulfate. The solvent was evaporated in vacuo and the residue was purified by flash chromatography using methanol in dichloromethane as the eluant to give the product as a colorless glass, 0.36 g (50%); IR(KBr); 3362, 2939, 1617, 1569 and 1496 cm$^{-1}$; MS: m/z 353 (MH+); $^1$H NMR(CDCl$_3$): δ 1.30 (s, 3H), 1.49 (s, 3H), 1.80–1.90 (m, 4H), 2.53 (m, 2H), 3.05–3.35 (m, 8H), 3.57 (d, J=4.6 Hz, 1H, exchanges with D$_2$O), 3.81 (dd, J=4.6 Hz, J=9.3 Hz, 1H), 5.86 (d, J=9.3 Hz, 1H), 6.83 (s, 1H).

Anal. calcd. for $C_{17}H_{24}N_2O_4S$: C, 57.93; H, 6.86; N, 7.95.

Found: C, 57.63; H, 6.77; N, 8.40.

EXAMPLE 99

N-Methoxy-N-methyl-3,3-dimethylacrylamide 3,3-Dimethylacryloyl chloride (28.2 mL, 0.253 mol) was slowly added to a mixture of N,O-dimethylhydroxylamine hydrochloride (27.2 g, 0.278 mol) and triethylamine (75 mL, 0.519 mol) in dichloromethane (300 mL) at 0° to 30° C. and stirred 1 h at 0° C. The resultant mixture was washed with 1 N hydrochloric acid and then with 1 N sodium hydroxide and dried over magnesium sulfate. The solvent was evaporated in vacuo and the residue vacuum distilled (60° to 70° C. at 0.2 mm Hg) to give the product, 26.8 g (74%) as a colorless oil; IR(neat): 2938 and 1660 cm$^{-1}$: MS: m/z 144 (MH+); $^1$H NMR(CDCl$_3$): δ 1.91 (d, J=1.2 Hz, 3H), 2.14 (d, J=0.9 Hz, 3H), 3.20 (s, 3H), 3.68 (s, 3H), and 6.12 (bs, 1H).

3-t-Butoxy-4-(3-methyl-1-oxo-2-buten-1-yl)thiophene (23)

t-Butyllithium (1.7 M in pentanes, 66 mL, 0.112 mol) was added to a solution of 4-bromo-3-t-butoxythiophene (Lawesson, S., Jakobsen, H. J., Tetrahedron, 1965, 21, 3331) (12.49 g, 53.1 mmol) at −75° C. and stirred for 1 h. N-methoxy-N-methyl-3,3-dimethylacrylamide (16.0 g, 0.112 mol) was added to the solution at −75° C. and the dry ice acetone bath was removed. The mixture was allowed to stir at ambient temperature overnight. The mixture was washed with 1 N hydrochloric acid and dried over magnesium sulfate. The solvent was evaporated in vacuo and the residue was purified by flash chromatography using 5% diethyl ether in pentanes as the eluant to give 23 as an amber oil, 12.25 g (97%); IR(neat): 2977, 1655, 1612, 1520 and 1470 cm$^{-1}$: MS: m/z 239 (MH+); $^1$H NMR (CDCl$_3$): δ 1.37 (d, 9H), 1.97 (d, J=1.1 Hz, 3H), 2.22 (d, J=1.1 Hz, 3H), 6.56 (d, J=3.6 Hz, 1H), 6.85 (bs, 1H) and 7.86 (d, J=3.6 Hz, 1H).

5,6-Dihydro-5,5-dimethyl-7H-thieno[3,4-b]pyran-7-one (24)

A solution of 3-t-butoxy-4-(3-methyl-1-oxo-2-buten-1-yl) thiophene (12.2 g, 51.2 mmol) and p-toluenesulfonic acid (0.5 g) in toluene was heated to reflux for 2 h. The solvent was evaporated in vacuo and the residue was purified by flash chromatography using 25% hexane in dichloromethane as the eluant to give 24 as a waxy tan solid, 5.9 g (63%); mp 42°–45 0C; IR(neat): 2977, 1692 and 1554 cm$^{-1}$; MS: m/z 183 (MH+); $^1$H NMR(CDCl$_3$): δ 1.44 (s,6H), 2.62 (s, 2H), 6.43 (d, J=3.3 Hz, 1H) and 8.00 (d, J=3.3 Hz, 1H).

Anal. calcd. for $C_9H_{10}O_2S$: C, 59.32; H, 5,53.

Found: C, 59.40; H, 5,58.

3-Bromo-5,6-dihydro-5,5-dimethyl-7H-thieno[3,4-b]pyran-7-one (25, $R_1$=Br)

N-Bromosuccinimide (15.0 g, 84.3 mmol) was added to a solution of 5,6-dihydro-5,5-dimethyl-7H-thieno-[3,4-b]pyran-7-one (15.0 g, 82.6 mmol) in dichloromethane (300 mL) at 0° C., and the resultant solution was stirred for 2 h at 0° C. The solution was washed with water and dried over magnesium sulfate. The solvent was evaporated in vacuo to give the product as a dark grey solid, 15.1 g (70%), mp 63°–72° C.; IR(neat): 1694, 1558 and 1438 cm$^{-1}$: MS: m/z 261 (MH+); $^1$H NMR(CDCl$_3$): δ 1.47 (s, 6H), 2.63 (s, 2H),7.99 (s, 1H).

Anal. calcd. for $C_9 H_9BrO_2S$: C, 41.40; H, 3.47.

Found: C, 41.30; H, 3.46.

3-Bromo-5,6-dihydro-7-hydroxy-5,5-dimethyl-7H-thieno[3,4-b]pyran -(26,$R_1$=Br)

Sodium borohydride (2.61 g, 69.0 mmol) was added to a solution of 3-bromo-5,6-dihydro-5,5-dimethyl-7H-thieno [3,4-b]pyran-7-one (12.63 g, 48.4 mmol) in ethanol (200 mL) at rt. The mixture was stirred at rt for 3 h and poured into ice water (600 mL) and extracted with diethyl ether. The organic phase was washed with water and dried over magnesium sulfate. The solvent was evaporated in vacuo to give the product as an amber oil, 12.06 g (95%); $^1$H NMR(CDCl$_3$): δ 1.32 (s, 3H), 1.50 (s, 3H), 1.60–2.20 (m, 3H), 4.81 (m, 1H) and 7.26 (s, 1H).

3-Bromo-5,5-dimethyl-5H-thieno[3,4-b]pyran (27, R₁=Br)

A solution of 3-bromo-5,6-dihydro-7-hydroxy-5,5-dimethyl-7H-thieno[3,4-b]pyran (12.06 g, 45.8 mmol) and p-toluenesulfonic acid (0.26 g, 1.37 mmol) in benzene (300 ml) was heated to reflux for 3 h in an apparatus fitted with a Dean-Stark trap to remove water. The resultant solution was cooled to rt and filtered through a pad of silica gel and the silica gel was washed with dichloromethane; the organic solutions were combined. The solvent was evaporated in vacuo to give the product as a brown oil, 10.23 g (91%); $^1$H NMR (CDCl₃): δ 1.38 (s,6H), 5.65 (d, J=14 Hz, $^1$H), 6.37 (d, J=14 Hz, $^1$H) and 6.87 (s, $^1$H).

trans-3,6-Dibromo-5,6-dihydro-7-hydroxy-5,5-dimethyl-7H-thieno[3,4-b]pyran (28, Ri =Br)

N-Bromosuccinimide (7.65 g, 43.0 mmol) was added in portions to a solution of 3-bromo-5,5-dimethyl-5H-thieno [3,4-b]pyran (10.23 g, 41.7 mmol) and water (1.13 mL, 62.6 mmol) in dimethyl sulfoxide (110 mL) at 20° C. The solution was stirred at rt for 1h and poured into water. The product was extracted into diethyl ether, washed several times with water and dried over magnesium sulfate. The solvent was evaporated in vacuo to give the product as a brown oil, 12.14 g (85%); IR(neat): 1572 and 1457 cm$^{-1}$: MS: m/z 341 (MH+) $^1$H NMR(CDCl₃): δ 1.42 (s,3H), 1.66 (s, 3H), 2.55 (bs, $^1$H, exchanges with D₂O), 4.02 (d, J=9.6 Hz, $^1$H), 4.86 (d, J=9.6 Hz, $^1$H) and 7.29 (s, $^1$H).

3-Bromo-5,6-dihydro-6,7-epoxy-5,5-dimethyl-7H-thieno [3,4-b]pyran (29, R₁=Br)

Sodium hydride (60% in mineral oil, 0.431 g, 10.8 mmol) was added to a solution of trans-3,6-dibromo-5,6-dihydro-7-hydroxy -5,5-dimethyl-7H-thieno[3,4-b]pyran (3.36 g, 9.81 mmol) in DMF (50ML) and stirred at rt for 2 h. The solution was poured into water (150 mL) and extracted with diethyl ether. The organic phase was washed several times with water and dried over magnesium sulfate. The solvent was evaporated in vacuo to give the product as a brown oil, 2.65 g. The oil was used without further purification. MS: m/z 261 MH+); $^1$H NMR(CDCl₃): δ 1.27 (s,3H), 1.62 (s, 3H), 3.39 (d, J=7 Hz, $^1$H), 3.98 (d, J=7 Hz, 1H) and 7.30 (s, $^1$H).

trans-7-Azido-3-bromo-5,6-dihydro-6-hydroxy-5,5-dimethyl-7H-thieno [3,4-b]pyran (20, R₃R₄N=N₃, R₁=Br)

Sodium azide (2.63 g, 40.6 mmol) was added to a mixture of 29 (R₁=Br) (2.65 g, 10.1 mmol) in acetone (40 mL) and water (20 mL) and stirred at rt for 2 h. The resultant solution was poured into water (200 mL) and extracted with diethyl ether. The organic phase was washed with water several times and dried over magnesium sulfate. The solvent was evaporated in vacuo to give an oil which crystallized from hexanes to give the product as a colorless solid, 2.0 g (65%): mp 80°-87° C. dec.; IR(KBr): 2106, 1576 and 1465 cm$^{-1}$: MS: m/z 304 (MH+); $^1$H NMR(CDCl₃): δ 1.28 (s,3H), 1.52 (s, 3H), 2.31 (d, J=4.9 Hz, $^1$H, exchanges with D₂O), 3.70 (dd, J=4.9 Hz, J=8.7 hz, $^1$H, simplifies to d, J=8.7 Hz, with D₂O exchange), 4.35 (dd, J=1.4 Hz, J=8.7 Hz, $^1$H) and 7.23 (d, J=1.4 Hz, $^1$H).

Anal. calcd. for C₉H₁₀BrN₃O₂S: C, 35.54; H, 3.31; N, 13.81.

Found: C, 35.77; H, 3.40; N,13.93.

trans-7-Amino-5,6-dihydro-6-hydroxy-5,5-dimethyl-7H-thieno [3,4-b]pyran (20, R₃R₄N=NH₂, R₁=H)

trans-7-Azido-3-bromo-5,6-dihydro-6-hydroxy-5,5-dimethyl-7H-thieno [3,4-b]pyran (5.32 g, 17.5 mmol) in tetrahydrofuran (60 mL) was slowly added to a suspension of lithium aluminum hydride (1.99 g, 52.5 mmol) in tetrahydrofuran (100 mL). The mixture was heated to reflux for 2 h. The reaction was carefully quenched by adding sequentially water (2 mL), aqueous sodium hydroxide (15%, 2 mL) and water (6 mL). The inorganics were removed by filteration and washed with dichloromethane. The combined organic layers were dried over magnesium sulfate. The solvent was evaporated in vacuo to give the product as a colorless solid, 3.07 g (88%), mp114°-116° C.; MS: m/z 200 (MH+); $^1$H NMR(CDCl₃): δ 1.22 (s,3H), 1.47 (s, 3H), 2.34 (bs, 3H, exchanges with D₂O), 3.36 (d, J=9.8 Hz, $^1$H), 3,66 (dd, J=1.4 Hz, J=9.8 Hz, $^1$H), 6.28 (d, J=3.4 Hz, $^1$H) and 7.10 (dd, J=1.4 Hz, J=3.4 Hz,1H).

trans-7-(5-Chloroventamido)-5,6-dihydro-6-hydroxy-5,5-dimethyl -7H-thieno[3,4-b]pyran 5-Chlorovaleryl chloride (2.04 mL, 15.8 mmol) was added dropwise to a solution of 20 (R₃R₄N=NH₂, R₁=H) (3.0 g, 15.1 mmol) and triethylamine (6.3 Ml, 45.2 mmol) in dichloromethane (50 mL) at 0° C. The solution was stirred at0° C. for 1 h. The solution was poured onto a silica gel column and the product purified by flash chromatography using 3% methanol in dichloromethane as the eluant to give the product as an amber oil, 4.83 g (100%); IR(KBr): 3294, 1645, 1561, 1541 and 1453 cm$^{-1}$; $^1$H NMR(CDCl₃): δ 1.27 (s,3H), 1.46 (s, 3H), 1.68–1.96 (m, 4H), 2.25–2.46 (m, 2H), 3.48–3.70 (m, 3H), 4.60 (bs, $^1$H), 4.97 (m, $^1$H), 6.20 (bd, $^1$H), 6.36 (d, J=3 Hz, $^1$H) and 7.08 (dd, J=1 Hz, J=3 Hz,1H).

trans-5,6-Dihydro-6-hydroxy-5,5-dimethyl-7-(2-oxopiperidin-1-yl) -7H-thieno[3,4-b]pyran Sodium hydride (60% in mineral oil, 0.634 g, 15.8 mmol) was added to a solution of trans-7-(5-chloropentamido)-5,6-dihydro-6-hydroxy -5,5-dimethyl-7H-thieno[3,4-b]pyran (4.8 g, 15.1 mmol) in DMF (50 mL) at 0° C. and stirred at 0° C. for 2 h. The solution was poured into water (250 mL) and extracted with dichloromethane. The organic phase was washed several times with water and poured onto a column of silica gel. The product was purified by flash chromatography using 3% methanol in dichloromethane as the eluant to give a solid which was triturated in diethyl ether to give the product as a colorless solid, 2.92 g (69%): mp 171°-172° C.; IR(KBr): 3430, 2973, 1613, 1563 and 1488 cm$^{-1}$; MS: m/z 282 (MH+); $^1$H NMR(CDCl₃): δ 1.27 (s,3H), 1.48 (s, 3H), 1.78–1.88 (m, 4H), 2.56 (m, 2H), 3.04 (m, $^1$H), 3.20 (m, 1h), 3.42 (d, J=4.9 Hz, $^1$H, exchanges with D₂O), 3.75 (dd, J=4.9 Hz, J=10.1 Hz, $^1$H), 5.83 (dd, J=1.4 Hz, J=10.1 Hz, $^1$H), 6.36 (d, J=3.4 Hz, $^1$H) and 6.86 (dd, J=1.4 Hz, J=3.4 Hz, $^1$H).

Anal. calcd. for C₁₄H₁₉ NO₃S: C, 59.76; H, 6.81; N, 4.98; S, 11.40.

Found: C, 59.79; H, 6.84; N, 4.87; S, 11.51.

EXAMPLE 100 trans-7-Amino-5,6-dihydro-6-hydroxy-5,5-dimethyl-7H-thieno [3,2-b]pyran dibenzoyl-L-tartrate A solution of 7-amino-5,6-dihydro-6-hydroxy-5,5-dimethyl-7H -thieno[3,2-b]pyran (1.73 g, 9.69 mmol)

was treated with dibenzoyl-L-tartaric acid (3.3 g, 8.69 mmol) and stirred at rt for 30 min. The mixture was concentrated in vacuo and recrystallized from ethanol to yield 1.8 g (37%) of trans-7-amino-5,6-dihydro-6-hydroxy-5,5-dimethyl-7H-thieno [3,2-b]pyran dibenzoyl-L-tartrate: mp 171°-172° C.; MS: m/z 200(MH+);a$_D$20°=−84.1° (MeOH).

Anal. Calcd. for $C_{27}H_{27}$ $NO_{10}S$: C,58.16; H,4.88; N,2.51.

Found: C, 57.90; H, 4.72; N, 2.41.

EXAMPLE 101 trans-7-Amino-5,6-dihydro-6-hydroxy-5,5-dimethyl-7H-thieno [3.2-b]pyran dibenzoyl-D-tartrate A solution of 7-amino-5,6-dihydro-6-hydroxy-5,5-dimethyl -7H-thieno[3,2-b]pyran (1.73 g, 9.69 mmol) was treated with dibenzoyl-D-tartaric acid (3.3 g, 8.69 mmol) and stirred at rt for 30 min. The mixture was concentrated in vacuo and recrystallized from ethanol to yield 2.1 g (43%) of trans-7-amino-5,6-dihydro-6-hydroxy-5,5-dimethyl -7H-thieno[3,2-b]pyran dibenzoyl-D-tartrate: mp 176°-177° C.; MS: m/z 200(MH+); a$_D$20°=+75.8° (MeOH)

Anal. Calcd. for $C_{27}H_{27}$ $NO_{10}S$: C,58.16; H,4.88; N,2.51.

Found: C, 58.14; H, 4.94; N, 2.58.

EXAMPLE 102

(−)-trans-5,6-Dihydro-6-hydroxy-5,5-dimethyl-2-nitro-7-(2-oxopiperidin-1-yl) -7H-thieno[3,2-b]pyran The (/)-trans-5,6-dihydro-6-hydroxy-5,5-dimethyl-2-nitro-7-(2-oxopiperidin-1-yl) -7H-thieno[3,2-b]pyran was resolved by a chiral HPLC method using a preparative Cyclobond I (beta-cyclodextrin) column (250×22.1 mm). The mobile phase was 0.01M ammonium acetate in acetonitrile (87:13). The wavelength monitored was 290 nm and flow rate was 7 ML/ min. The (−) enantiomer was isolated at a retention time of approximately 25 minutes. Recrystallization from methanol/diethylether gave the title compound as a yellow solid; mp 160-162 ↓ C; [a]S(20/φ) (CHCl₃)=−53.8 ; ¹H NMR (CDCl₃): d 1.32 (s, 3H), 1.51 (s, 3H),1.89 (m, 4H),2.52 (m, 2H),3.21 (m, 2H),3.86-3.81 (dd, J=3,2Hz, ¹H), 3.98 (d, J=2.1Hz, 1H),5.86 (d, J=3,2Hz, ¹H),7.39 (s,1H). MS:m/z 327 MH+)

Anal.Calcd. for $C_{14}H_{18}N_2O_5S$: C, 51.52; H, 5,56; N, 8.58.

Found: C, 51.44; H, 5.39; N, 8.40.

EXAMPLE 103

(+)-trans-5,6-Dihydro-6-hydroxy-5,5-dimethyl-2-nitro-7-(2-oxopiperidin-1-yl) -7H-thieno[3,2-b]pyran The title compound was prepared as described in example 102. The (+) enantiomer was isolated at a retention time of approximately 20 minutes. Recrystallization from methanol/diethylether gave the title compound as a yellow solid; m.p.158°-160 C.; [a]S(20/φ) (CHCl₃)=+41.6 ; ¹H NMR (CDCl₃): d 1.32 (m, 3H),1.52 (s, 3H), 1.93-1.75 (m, 4H),2.52 (m, 2H),3.21 (m, 2H),3.86-3.81 (dd, J=3,2Hz, ¹H),4.11 (d, J=2.2Hz, ¹H),5.86 (d, J=3.1Hz, 1H),7.39 (s, ¹H). MS: m/z 327 MH+).

Anal.Calcd. for $C_{14}H_{18}N_2O_5S$: C, 51.52; H, 5,56; N, 8.58.

Found: C, 51.68; H, 5.72; N, 8.19.

EXAMPLE 104

3-Bromo-2-t-butoxythiophene

A −78° C. solution of 2,3-dibromothiophene (Aldrich, 10.0 g, 41.3 mmol) in 150 mL of diethyl ether was treated with n-butyl lithium (2.5 M, 16.5 mL) over a 20 min period. The mixture was stirred 1h at −78° C. Magnesium bromide (13.0 g, 49.6 mmol) was added as a solid in two portions. The mixture was stirred at −780° C. for 1h and rt for 2h. t-Butylperbenzoate was added at 0° C. and the reaction was allowed to stir at ambient temperature overnight. The mixture was quenched with ice water (50 mL) and 2N HCl (25 mi). The organic layer was separated and washed once with ice cold 1 N NAOH, water and brine. The organic layer was dried over magnesium sulfate and concentrated to give 10.5 g (98%) of the title compound: MS: m/z 236 MH+); ¹H NMR(CDCl₃): d 1.36 (s, 9H), 6.61 (d, j=6.1 Hz, ¹H) and 7.23 (d, J=6.1 Hz, 1H).

2-t-Butoxy-3-(3-methyl-1-oxo-2-b@n-1-yl)thioohene (11)

A −78° C. solution of 3-bromo-2-t-butoxythiophene (9.5 g, 41.5 mmol) in 200 mL of diethyl ether was treated with t-butyl lithium (1.7 M, 27.5 mL) over a 20 min period. The mixture was stirred at −78° C. for 1h then treated with N-methoxy-N-methyl-3,3-dimethylacrylamide (18.0 g, 127.0 mmol) as prepared in Example 99. The mixture was allowed to warm to rt overnight. The reaction was poured into ice cold 1N HCl (200 mL) and the organic layer was separated then dried over magnesium sulfate. The filtrate was concentrated in vacuo and the resulting oil was purified by flash chromatography (silica gel, dichloromethane) to give 3.5 g (37%) of 11: MS: m/z 239(MH+); ¹H NMR(CDCl₃): d 1.42 (s, 9H), 1.99 (s, 3H), 2.01 (s, 3H), 6.63 (d, J=6.1 Hz, ¹H), 6.89 (s, ¹H) and 7.25 (d, J=6.1 Hz, ¹H).

5,6-Dihydro-6,6-dimethyl-4H-thieno[2,3-b]pyran-4-one (12)

A solution of 11 (2.5 g, 10.5 mmol) in toluene (50 mL) and catalytic p-toluene sulfonic acid was heated to reflux for 3 h. The mixture was concentrated and the resulting oil was purified by flash chromatography (silica gel, dichloromethane) to give 1.1 g (58%) of 12: MS: m/z 183MH+); ¹H NMR(CDCl₃): d 1.53 (s, 6H), 2.62 (s, 2H), 6.46 (d, J=6.1 Hz, ¹H) and 7.05 (d, J=6.1 Hz, ¹H).

Anal. Calcd. for $C_9H_{10}O_2S$: C, 59.32; H, 5,53.
Found: C, 59.33; H, 5.67.

2,5-Dibromo-5,6-dihydro-6,6-dimethyl-4H-thieno[2,3-b]pyran-4-one (13)

Bromine (4.2 ml, 82.4 mmol) was added dropwise to a solution of 12 (7.5 g, 41.2 mmol) in acetic acid (70 ml) at rt. After 1 h, the solution was poured into water (300 ml). The product was extracted with dichloromethane (100 ml), washed with water then saturated aqueous sodium bicarbonate and dried over magnesium sulfate. The solvent was evaporated in vacuo, and the residue was purified by flash chromatography (silica gel, 5% ether in pentanes) to give 8.1 g (58%) of 11 as an orange solid: mp 97-99° C.; ¹H NMR (CDCl₃): d 1.61 (s, 3 H), 1.69 (s, 3 H), 4.20 (s, 1 H) and 7.10 (s, 1 H); IR (KBr): 1687, 1527 and 1491 cm⁻¹; MS: m/z 339 MH+).

Anal. Calcd. for $C_9H_8Br_2O_2S$: C, 31.79; H, 2.37.
Found: C, 31.98; H, 2.38.

cis-2,5-Dibromo-5,6-dihydro-4-hydroxy-6,6-dimethyl-4H-thieno [2,3-b]pyran(14).

Sodium borohydride (1.0 g, 26.4 mmol) was added to a solution of 13 (2.5 g, 7.35 mmol) in ethanol (30 ml) and stirred for 16 h. The solution was poured into water (200 ml). The product was extracted with dichloromethane (50 ml), washed several times with water and dried over magnesium sulfate. The solvent was evaporated in vacuo to give the product as an amber oil, 1.69 g (67%), which was used without further purification. $^1$H NMR(CDCl$_3$): d 1.52 (s, 3 H), 1.61 (s, 3 H), 2.42 (d, J=9.5 Hz, 1 H), 4.34 (d, J=4.4 Hz, 1 H), 4.70 (d of d, i =9.5 and 4.4 Hz, 1 H) and 6.81 (s, 1 H); IR(neat): 3600–3200,1566 and 1467 cm$^{-1}$; MS: m/z 342 MH+).

cis-2,5-Dibromo-4-chloro-5,6-dihydro-6,6-dimethyl-4H-thieno [2,3-b]pyran(15)

Thionylchloride (1.8 ml, 24.6 mmol) was added to a solution of 14 (1.7 g, 4.9 mmol) in dichloromethane (30 ml) and stirred for 1 h. The solution was washed with saturated aqueous sodium bicarbonate (2×300 ml) and dried over magnesium sulfate. The solvent was evaporated in vacuo to give 15 as a yellow oil 1.7 g (96%), which was used without further purification. $^1$H NMR(CDCl$_3$): d 1.51 (s, 3 H), 1.66 (s, 3 H), 4.27 (d, J=6,7 Hz, 1 H), 5.10 (d, J=6.7 Hz, 1 H) and 6.78 (s, 1 H); IR (neat) 1566 and 1472 cm$^{-1}$; MS: m/z 356 MH+).

trans-2,5-Dibromo-5,6-dihydro-4-hydroxy-6,6-dimethyl-4H-thieno [2,3-b]pyran (16).

Silica gel, 230–400 mesh, (1.0 g) was added to a solution of 15 (1.6 g, 4.6 mmol) in 5% ether in pentanes (30 ml). The resultant mixture was stirred at rt for 30 min. and filtered through a pad of silica gel. The silica gel pad was eluted with 5-20% ether in pentanes until all the product had been removed. The combined fractions were evaporated in vacuo to give 16 as an amber oil 1.1 g (73%). $^1$H NMR (CDCl$_3$): d 1.52 (s, 3 H), 1.60 (s, 3 H), 2.43 (d, J=5.0 Hz, 1 H), 4.06 (d, J=7.1 Hz, 1 H), 4.76 (d of d, J=5.0 and 7.1 Hz, 1 H) and 6.80 (s, 1 H); IR (neat): 3600–3200, 1570 and 1469 cm$^{-1}$; MS: m/z 342 (MH+).

trans-4-Azido-2-bromo-5,6-dihydro-5-hydroxy-6,6-dimethyl-4H-thieno [2.3-b]pyran (18)

Sodium hydride, 60% in mineral oil, (134 mg, 3.36 mmol) was added to a solution of 16 (1.15 g, 3.36 mmol) in N,N-dimethylformamide (25 ml) at 0° C. and stirred at rt for 2 h. The reaction was cooled to 0° C. and sodium azide (635 mg, 10.8 mmol) in water (2 ml) was added. After stirring at rt for 1 h, the resultant solution was poured into water (150 ml). The product was extracted with dichloromethane (50 ml), washed several times with water and dried over magnesium sulfate. The solvent was evaporated in vacuo to give the product as a brown oil, 1.0 g (98%), which was used without further purification. $^1$H NMR (CDCl$_3$): d 1.31 (s, 3 H), 1.48 (s, 3 H), 2.42 (d, J=5.3 Hz, H), 3.72 (d of d, J=7.5 and 5.3 Hz, 1 H), 4.21 (d, J 7.5 Hz, 1 H) and 6,76 (s, 1 H); IR (neat) 3600–3200, 2101, 1663, 1568 and 1470 cm$^{-1}$; MS: m/z 303 MH+).

trans-4-Amino-5,6-dihydro-5-hydroxy-6,6-dimethyl-4H-thieno [2.3-b]pyran (19, (R$_1$, R$_2$, R$_3$, R$_4$=H)

A solution of 18 (1.0 g, 3.3 mmol) in tetrahydrofuran (10 ml) was added to a mixture of lithium aluminum hydride (0.37 g, 9.9 mmol) in tetrahydrofuran (50 ml). The mixture was heated to reflux for 2 h. The reaction was quenched by careful sequential addition of water (0.4 ml), 15% aqueous sodium hydroxide (0.4 ml) and water (1.2 ml). Magnesium sulfate was added to the mixture and the inorganics were removed by filtration. The inorganics were washed with dichloromethane, and the combined solutions were evaporated in vacuo to give 19 (R$_1$, R$_2$, R$_3$, R$_4$=H) as a colorless solid, 0.59 g (90%). $^1$H NMR (CDCl$_3$): d 1.26 (s, 3H), 1.50 (s, 3H), 2.05 (br s, 3H), 3.36 (d, J=8.8 Hz, 1 H), 3.56 (d, J=8.8 Hz, $^1$H), 6.46 (d, J=5.8 Hz, $^1$H), and 6,71 (d, J=5.8 Hz, $^1$H); IR (neat): 3400–2700, 1567 and 1456 cm$^{-1}$; MS: M/Z 200 (MH+).

trans-4-(5-Chloroventamido)-5,6-dihydro-5-hydroxy-6,6-dimethyl -4H-thieno[2,3-b]pyran (19, (R$_1$, R$_2$, R$_3$,=H, R$_4$=C(O)(CH$_2$)$_4$Cl).

5-Chlorovaleryl chloride (0.42 ml, 3.25 mmol) was added to a solution of 19 (R$_1$, R$_2$, R$_3$, R$_4$=H) (0.59 g, 2.96 mmol) and triethylamine (1.44 ml, 10.4 mmol) in dichloromethane (25 ml) at 0° C. and stirred at rt for 1 h. The product was purified by flash chromatography (silica gel, 2.5% methanol in dichloromethane) to give the title compound as an amber oil, 0.76 g (81%). $^1$H NMR(CDCl$_3$): d 1.31 (s, 3H), 1.48 (s, 3H), 1.83–1.88 (m, 4H), 2.25–2.30 (m, 2 H), 3.54–3.60 (M, 2H), 3,65 (d, J=8.1 Hz, $^1$H), 4.83 (d of d, $^1$H), 5.84 ( br d, $^1$H, exchanges with D$_2$O), 6.51 (d, J=5.8 Hz, $^1$H), 6.61 (d, J=5.8 Hz, $^1$H) and 8.45 (br s, $^1$H, exchanges with D$_2$O); MS: m/z 318 MH+).

trans-5,6-dihydro-5-hydroxy-6.6-dimethyl-4-(2-oxoniveridin-1-yl) -4H-thieno[2.3-b]pyran.

Sodium hydride, 60% in mineral oil, (104 mg, 2.60 mmol) was added to a solution of 19 (R$_1$, R$_2$, R$_3$, =H, R$_4$ =C(O)(CH$_2$)$_4$Cl) (0.75 g, 2.36 mmol) in N,N-dimethylformamide (25 ml) at 0° C. and stirred at rt for 1 h. The resultant solution was poured into water (200 ml). The product was extracted with dichloromethane, washed several times with water and purified by flash chromatography (silica gel, 2.5% methanol in dichloromethane). The product was crystallized from ether to give colorless crystals, 0.47 g (71%): mp 160°–161° C.; $^1$H NMR(CDCl$_3$): d 1.32 (s, 3H), 1.50 (s, 3H), 1.74–1.87 (m, 4H), 2.50–2.56 (m, H), 3.03–3.20 (m, 2H), 3.74–3.81 (m, 2H, collapses to a d, J=9.5 Hz, $^1$H with D$_2$O), 5.64 (d, J=9.5 Hz, $^1$H), 6.44 (d, J=5.8 Hz, $^1$H) and 6.48 (d, J=5.8 Hz, 1 H); IR(KBr): 3328, 1607, 1563 and 1490 cm$^{-1}$; MS: m/z 282 (MH+).

Anal. calcd. for C$_{14}$H$_{19}$ NO$_3$S: C, 59.76; H, 6.81; N, 4.98; S, 11.40.

Found: C, 59.73; H, 6.93; N, 4.89; S, 11.30.

EXAMPLE 105 trans-2-Chloro-5,6-dihydro-5-hydroxy-6,6-dimethyl-4-(2-oxopineridin-1-yl) -4H-thieno[2.3-b]pyran A solution of sulfuryl chloride, 1.0 M in dichloromethane, (1.2 ml, 1.2 mmol) was added to a solution of trans-5,6-dihydro-5-hydroxy-6,6-dimethyl-4-(2-oxopiperidin-1-yl) -4H-thieno[2,3-b]pyran (0.30 g, 1.06 mmol) in dichloromethane (25 ml) at 0° C., and stirred at rt for 2 h. The product was purified by flash chromatography (silica gel, 2.5% methanol in dichloromethane) to give the title compound as a colorless solid 0.25 g (75%): mp 195°–196° C.; $^1$H NMR(CDCl$_3$): d 1.33 (s, 3H), 1.48 (s, 3H), 1.77–1.87 (m, 4H), 2.50–2.56 (m, 2H), 3.03 –3.20 (m, 2H), 3.74–3.81 (m, 2H, collapses to a doublet, $^1$H, with D$_2$O), 5,58 (d, J=9.2 Hz, $^1$H) and 6.31

(s, 1H); IR (KBr): 1613, 1599, 1572 and 1490 cm$^{-1}$; MS: m/z 316 MH+).

Anal calcd for $C_{14}H_{18}ClNO_3S$: C, 53.24; H, 5.74; N, 4.43.

Found: C, 53.22; H, 5,59; N, 4.10.

EXAMPLE 106 trans-2-Bromo-5,6-dihydro-5-hydroxy-6,6-dimethyl-4-(2-oxoniperidin-1-yl)-4H-thieno[2,3-b]pyran The title compound was prepared by the method described in Example 4 starting with trans-5,6-dihydro-5-hydroxy-6,6-dimethyl -4-(2-oxopiperidin-1-yl)-4H-thieno[2,3-b]pyran: mp 167°–169° C.

Anal. Calcd for $C_{14}H_{18}BRNO_3S$: C, 46.67; H, 5.04; N, 3.89.

Found: C,46.49; H, 4.97; N, 3.86.

EXAMPLE 107 trans-2-Carbomethoxy-5,6-dihydro-5-hydroxy-6.6-dimethy-4-(2-oxopiperidin-1-yl)-4H-thieno[2,3-b]pyran The title compound was prepared by the method described in Example 91 starting with trans-2-bromo-5,6-dihydro-5-hydroxy-6,6-dimethyl-4-(2-oxopiperidin-1-yl)-4H-thieno [2,3-b]pyran: mp 195°–197° C.

Anal. Calcd for $C_{16}H_{21}NO_5S$: C, 56.62; H, 6.24; N, 4.13.

Found: C, 56.80; H, 6.35; N, 4.07.

EXAMPLE 108 trans-2-Acetyl-5,6-dihydro-5-acetoxy-6,6-dimethyl-4-(2-oxopiperidin-1-yl) -4H-thieno[2,3-b]pyran The title compound was prepared by the method described in Example 6 starting with trans-5,6-dihydro-5-hydroxy-6,6-dimethyl -4-(2-oxopiperidin-1-yl)-4H-thieno[2,3-b]pyran: mp 180°–1810C.

Anal. Calcd for $C_{18}H_{23}NO_5S$: C, 59.16; H, 6.34; N, 3.83.

Found: C, 58.82; H, 6.33; N, 3.77.

EXAMPLE 109 trans-2-Acetyl-5,6-dihydro-5-hydroxy-6,6-dimethyl-4-(2-oxoniperidin-1-yl) -4H-thieno[2,3-b]pyran The title compound was prepared by the method described in Example 7 starting with trans-2-acetyl-5,6-dihydro-5-acetoxy-6,6-dimethyl-4-(2-oxopiperidin-1-yl)-4H-thieno [2,3-b]pyran: mp 166°–172° C.

Anal. Calcd for $C_{16}H_{21}NO_4S$: C, 59.42; H, 6.54; N, 4.33.

Found: C, 59.29; H, 6.40; N, 4.46.

EXAMPLE 110

Antihypertensive Activity

Antihypertensive activity was assessed using a direct measurement of mean arterial blood pressure in spontaneously hypertensive rats (SHR). On the day of the experiment, catheters were implanted into the left carotid artery and the left jugular vein of SHR under light ether anesthesia. The catheters were exteriorized at the nape of the neck and secured with an adhesive wrap. Animals were then placed in stainless steel restraint cages in a quiet room and allowed at least 90 min postsurgical recovery before recordings were collected. Recordings of arterial pressure were obtained using a Statham pressure transducer connected to a Gould 2800 chart recorder. Groups of 4–6 SHR received a single oral dose of drug or vehicle (0.5% methylcellulose) administered by gavage at doses of 0.03 to 20 mg/kg. The percent reduction of mean arterial blood pressure compared to controls is reported.

EXAMPLE 111

Rb$^{86}$ Efflux from Smooth Muscle

Rabbit aorta are removed from freshly sacrificed animals. The vessels are cleaned and cut into small circular rings. The rings are placed onto stainless steel wires and immersed in a biological buffer (37° C.) bubbled with 95% $O_2$/5% $CO_2$. Rb$^{86}$ (4–5 mCi/mL) is added to 40-50 mL buffer containing all of the aortic rings. This loads each ring with an approximately equal amount of Rb$^{86}$. After 3–4 hours, sets of 2 rings are placed into 4 mL vials of fresh buffer. A background efflux rate is determined over a 30–40 minute period. Test compound is then added to a number of the vials (usually five) as the rings are moved through the 4 mL solutions over a set time period (usually 10 minutes). Finally, the rings are placed into the vials containing no test compound for a period of 10–20 minutes. At the completion of the experiment, the tissues are digested overnight in Prostol before placing into scintillation cocktail to determine the total amount of radioactivity remaining within the tissues. An aliquot is removed from each of the efflux vials and quantitated in a liquid scintillation spectrometer. An efflux rate (or % change from predrug rates) is calculated and followed with time in the presence and absence of test compounds.

The pharmacological activity of the thienopyran derivatives is summarized below. Blood pressure reduction was measured in the spontaneously hypertensive rats (SHR). The Rb$^{86}$ efflux assay is a measure of potassium ion permeability changes within vascular smooth muscle cells.

TABLE

Biological Activity of Thienopyran Derivatives

| EX. | NR$_3$R$_4$ | R$_6$ | R$_2$ | DOSE$^a$ | SHR$^b$ | DOSE$^c$ | %$^d$ |
|---|---|---|---|---|---|---|---|
| 1 | pyrrolidinon-1-yl | OH | H | 20 po | −55% | 100 | 25% |
| 4 | pyrrolidinon-1-yl | OH | 2-Br | 20 po | −43% | 100 | 90% |
| 5 | pyrrolidinon-1-yl | OH | 2-NO$_2$ | 20 po | −60% | 100 | 114% |
| 2 | piperidon-1-yl | OH | H | 20 po | −53% | 100 | 40% |
| 8 | pyrrolidinon-1-yl | OAc | H | 20 po | −10% | | |
| 6 | pyrrolidinon-1-yl | OAc | 2-Ac | 20 po | −33% | 100 | 23% |
| 7 | pyrrolidinon-1-yl | OH | 2-Ac | 20 po | −62% | 100 | 57% |
| 9 | p-NO$_2$PhCONH | OH | 2-NO$_2$ | 20 po | −29% | 100 | 30% |
| 17 | p-CF$_3$PhCONH | OH | 2-NO$_2$ | 20 po | −14% | | |
| 12 | p-NO$_2$PhCONH | OAc | 2-Ac | 20 po | −20% | | |
| 14 | p-ClPhCONH | OH | H | | | | |
| 13 | p-NO$_2$PhCONH | OH | 2-Ac | 20 po | −63% | 100 | 26% |
| 15 | p-ClPhCONH | OH | 2-NO$_2$ | 20 po | −42% | 100 | 39% |
| 19 | homopiperidinon-1-yl | OH | H | 20 po | −12% | | |

TABLE-continued
Biological Activity of Thienopyran Derivatives

| EX. | NR$_3$R$_4$ | R$_6$ | R$_2$ | DOSE$^a$ | SHR$^b$ | DOSE$^c$ | %$^d$ |
|---|---|---|---|---|---|---|---|
| 10 | piperidon-1-yl | OH | 2-NO$_2$ | 20 po | −65% | | |
| 24 | pyrrolidinon-1-yl | OBz | H | 20 po | −12% | | |
| 20 | homopiperidinon-1-yl | OH | 2-NO$_2$ | 20 po | −34% | | |
| 18 | pyrrolidin-1-yl | OH | H | 100 po | −48% | | |
| 11 | piperidon-1-yl | OH | 2-Br | 20 po | −64% | | |
| 21 | 2-oxohexamethylene-imin-1-yl | OAc | H | 20 po | −9% | | |
| 31 | p-CF$_3$PhCONH | OH | 2-Ac | 20 po | −26% | | |
| 35 | p-FPhCONH | OH | H | 20 po | −8% | | |
| 52 | 3-pyridylCONH | OH | 2-NO$_2$ | 20 po | −54% | 100 | 19% |
| 53 | m-ClPhCONH | OH | 2-NO$_2$ | 20 po | −60% | | |
| 54 | p-FPhCONH | OH | 2-NO$_2$ | 1 po | −60% | | |
| 55 | p-MeOPhCONH | OH | 2-NO$_2$ | 20 po | −32% | | |
| 56 | m-FPhCONH | OH | 2-NO$_2$ | 20 po | −55% | | |
| 57 | p-MePhCONH | OH | 2-NO$_2$ | 20 po | −10% | | |
| 58 | m,p-F$_2$PhCONH | OH | 2-NO$_2$ | 20 po | −63% | | |
| 59 | 2-thenoylNH | OH | 2-NO$_2$ | 20 po | −17% | | |
| 60 | 2-furoylNH | OH | 2-NO$_2$ | 20 po | −43% | | |
| 61 | o-FPhCONH | OH | 2-NO$_2$ | 20 po | −56% | | |
| 65 | 2-oxopyridin-1-yl | OH | 2-NO$_2$ | 20 po | −57% | | |
| 66 | 2-isoindolone | OH | 2-NO$_2$ | 20 po | −61% | | |
| 67 | 3-pyridylCONH | OAc | 2-Ac | 20 po | −29% | | |
| 68 | 2-Ac | OAc | 2-Ac | 20 po | −21% | | |
| 69 | p-FPhCONH | OH | 2-Ac | 20 po | −75% | 30 | 27% |
| 70 | PhCONH | OH | 2-Ac | 20 po | −55% | | |
| 71 | m-ClPhCONH | OH | 2-Ac | 20 po | −59% | | |
| 72 | m,p-F$_2$PhCONH | OH | 2-Ac | 20 po | −62% | | |
| 73 | p-ClPhCONH | OAc | 2-Ac | 20 po | −40% | | |
| 74 | p-ClPhCONH | OH | 2-Ac | 20 po | −60% | | |
| 75 | p-MeOPhCONH | OH | 2-Ac | 20 po | −20% | | |
| 76 | o,p-F$_2$PhCONH | OH | 2-Ac | 20 po | −59% | 30 | 43% |
| 77 | o-FPhCONH | OH | 2-Ac | 20 po | −59% | | |
| 78 | m-NO$_2$PhCONH | OH | 2-Ac | 20 po | −63% | | |
| 79 | p-MePhCONH | OH | 2-Ac | 20 po | −10% | | |
| 80 | isonicotinamido | OAc | 2-Ac | 20 po | −14% | | |
| 81 | pyrrolidinon-1-yl | OMe | 2-Ac | 20 po | −67% | | |
| 82 | pyrrolidinon-1-yl | OH | 2-CF$_3$CO | 20 po | −68% | | |
| 83 | acetamido | OH | 2-Ac | 20 po | −65% | 100 | 57% |
| 84 | piperidon-1-yl | OH | 2-Ac | 20 po | −67% | 100 | 26% |
| 85 | 2-isoindolone | OH | 2-Ac | 20 po | −54% | | |
| 86 | p-FPhCONH | OH | 2-Br | 20 po | −53% | 30 | 36% |
| 87 | p-ClPhCONH | OH | 2-Br | 20 po | −16% | | |
| 88 | p-FPhSO$_2$NH | OH | 2-Br | 20 po | −11% | | |
| 89 | pyrrolidinon-1-yl | OAc | 2-Br | 20 po | −13% | 100 | 21% |
| 90 | piperidon-1-yl | OMe | 2-Br | 20 po | −45% | 100 | 54% |
| 91 | piperidon-1-yl | OH | 2-CO$_2$Me | 20 po | −37% | 100 | 63% |
| 92 | piperidon-1-yl | OH | 2-CONH$_2$ | 20 po | −68% | 100 | 92% |
| 93 | piperidon-1-yl | OH | 2-CO$_2$H | 20 po | −9% | | |
| 94 | piperidon-1-yl | OBn | 2-Br | 20 po | −35% | | |
| 95 | piperidon-1-yl | OBn | 2-CO$_2$Me | 20 po | −15% | | |
| 96 | piperidon-1-yl | OBn | 2-CONH$_2$ | 20 po | −56% | | |
| 97 | piperidon-1-yl | OH | 2-CN | 20 po | −66% | | |
| 98 | piperidon-1-yl | OH | 2-CONMe$_2$ | 20 po | −63% | 100 | 32% |
| 99 | piperidon-1-yl | OH | H | 20 po | −49% | 30 | 37% |
| 102 | (−)piperidon-1-yl | OH | 2-NO$_2$ | 0.1 po | −63% | | |
| 103 | (+)piperidon-1-yl | OH | 2-NO$_2$ | 3.0 po | −38% | | |
| 104 | piperidon-1-yl | OH | H | 20 po | −43% | | |
| 105 | piperidon-1-yl | OH | 2-Cl | 20 po | −67% | | |
| 106 | piperidon-1-yl | OH | 2-Br | 20 po | −67% | | |
| 107 | piperidon-1-yl | OH | 2-CO$_2$Me | 20 po | −68% | | |
| 108 | piperidon-1-yl | OAc | 2-Ac | 20 po | 67% | | |
| 109 | piperidon-1-yl | OH | 2-Ac | 20 po | −61% | | |

$^a$Dose of test compound in groups of 3–6 spontaneously hypertensive rats (SHR) administered po, mg/kg
$^b$% Decrease in mean arterial Concentration pressure compared to pretreatment control values
$^c$Concentration of test compound in ?M
$^d$% Increase of Rb$^{86}$ efflux from smooth muscle.

What is claimed is:
1. A compound of the formula:

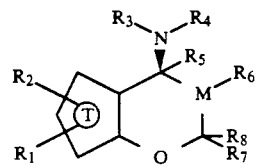

wherein

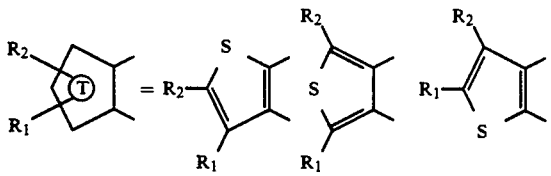

and $R_1$ and $R_2$ are selected from hydrogen, nitro, cyano, trifluoromethyl, halogen, lower alkyl ($C_{1-4}$), alkanoyl ($C_{2-4}$), substituted alkanoyl ($C_{2-4}$), wherein the substituent is halogen; benzoyl, substituted benzoyl, wherein the substituent is selected from bromo, chloro, iodo, alkyl ($C_{1-4}$), alkoxy ($C_{1-4}$), acyl ($C_{2-4}$), nitro, cyano and trifluoromethyl; acylamino ($C_{2-4}$), alkoxy carbonyl ($C_{1-4}$), CHO, COOH, $CONH_2$, $CON(R)_2$ and NHCOR wherein R is alkyl ($C_{1-4}$), alkoxy ($C_{1-4}$), phenyl or substituted phenyl wherein the substituent is selected bromo, chloro, iodo, lower alkyl, lower alkoxy, nitro, cyano, trifluoromethyl and acyl ($C_{2-4}$); $R_3$ and $R_4$ are selected from hydrogen, hydroxy, alkanoyl ($C_{2-5}$), alkyl ($C_{1-4}$), cycloalkyl ($C_{3-6}$), cycloalkyl carbonyl ($C_{3-6}$), pyridyl carbonyl, benzoyl, substituted benzoyl wherein the substituent is selected from brommo, chloro, iodo, alkyl ($C_{1-4}$), alkoxy ($C_{1-4}$), acyl ($C_{2-4}$), nitro, cyano and trifluoromethyl; or $R_3R_4N$ together are a heterocyclic ring selected from a pyrrole, pyrrolidine or piperidine ring; a ($C_{3-9}$) lactam selected from the group consisting of isoindolone, pyrrolidinone, piperidinone, pyridinone, pyrazinone, and glycine anhydride; or substituted ($C_{3-9}$) lactam; $R_5$ is hydrogen or together with $R_6$ forms a double bond; m is CH or taken together with $R_6$ is carbonyl; $R_6$ is hydroxy, alkoxy ($C_{1-6}$), alkanoyloxy ($C_{2-7}$), benzoyloxy, substituted benzoyloxy; and $R_7$ and $R_8$ are hydrogen or alkyl ($C_{1-4}$) or together form a ring having 5-8 carbon atoms; and optical isomers thereof.

2. A compound of claim 1 wherein $R_1$ and $R_2$ are hydrogen, halogen, nitro or alkanoyl; $R_3$ and $R_4$ are hydrogen, alkanoyl ($C_{2-5}$), alkyl ($C_{1-4}$), cycloalkyl ($C_{3-6}$), cycloalkyl carbonyl ($C_{3-6}$), benzoyloxy or substituted benzoyloxy; $R_5$ is hydrogen or together with $R_6$ forms a double bond; $R_6$ is hydrogen, hydroxy, alkoxy ($C_{1-6}$), or alkanoyloxy ($C_{1-4}$) and $R_7$ and $R_8$ are hydrogen or alkyl ($C_{1-4}$).

3. A compound of claim 1 selected from the group consisting of trans-5,6-Dihydro-6-hydroxy-5,5-dimethyl-7-nicotinamido-2-nitro-7H-thieno[3,2-b]pyran, trans-7-(3-chlorobenzamido)-5,6-dihydro-6-hydroxy-5,5-dimethyl-2-nitro-7H-thieno[3,2-b]pyran, trans-7-(4-fluorobenzamido)-5,6-dihydro-6-hydroxy -5,5-dimethyl-2-nitro-7H-thieno[3,2-b]pyran, trans-7-(3,4-difluorobenzamido)-5,6-dihydro-6-hydroxy-5,5-2-nitro-7H-thieno[3,2-b]pyran, dimethyl-2 trans-5,6-dihydro-6-hydroxy-7-(2-isoindolino)-5,5-dimethyl-2-nitro-7H-thieno[3,2-b]pyran, trans-2-acetyl-7-(4-fluorobenzamido)-5,6-dihydro-6-hydroxy-5,5-dimethyl-7H-thieno[3,2-b]pyran, trans-2-acetyl-7-(4-chlorobenzamido)-5,6-dihydro-6-hydroxy-5,5-dimethyl-7H-thieno[3,2-b]pyran, trans-2-acetyl-7-(2,4-difluorobenzamido)-5,6-dihydro-6-hydroxy -5,5-dimethyl-7H-thieno[3,2-b]pyran, trans-2-acetyl-5,6-dihydro-6-hydroxy-5,5-dimethyl-7-(3-nitrobenzamido) -7H-thieno[3,2-b]pyran, trans-2-trifluoromethylacetyl-5,6-dihydro-6-hydroxy-5,5-dimethyl -7-(2-oxopyrrolidin-1-yl)-7H-thieno[3,2-b]pyran, trans-2-Acetyl-7-acetamido-5,6-dihydro-6-hydroxy-5,5-dimethyl -7H-thieno[3,2-b]pyran, trans-2-acetyl-5,6-dihydro-6-hydroxy-5,5-dimethyl-7-(2-oxopiperidin -1-yl)-7H-thieno[3,2-b]pyran, trans-2-bromo-7-(4-fluorobenzamido)-5,6-dihydro-6-hydroxy-5, 5-dimethyl-7H-thieno[3,2-b]pyran, trans-2-bromo-5,6-dihydro-6-methoxy-5,5-dimethyl-7-(2-oxopiperidin-1-yl)-7H-thieno[3,2-b]pyran, and trans-2-cyano-5,6-dihydro-6-hydroxy-5,5-dimethyl-7-(2-oxopiperidin-1-yl)-7H-thieno[3,2-b]pyran and the optical isomers thereof.

4. A compound of claim 1 which is (−)-trans-5,6-Dihydro-6-hydroxy-5,5-dimethyl-2-nitro-7-(2-oxopiperidin-1-yl)-7H-thieno[3,2-b]pyran.

5. A compound of claim 1 selected from the group consisting of trans-5,6-Dihydro-5-hydroxy-616-dimethyl-4-(2-oxopiperidin-1-yl)-4H-thieno[2,3-b]pyran; trans-2-chloro-5,6-dihydro-5-hydroxy-6,6-dimethyl-4-(2-oxopiperidin-1-yl)-4H-thieno[2,3-b]pyran; trans-2-bromo-5,6-dihydro-5-hydroxy-6,6-dimethyl-4-(2-oxopiperidin-1-yl)-4H-thieno[2,3-b]pyran; trans-2-carbomethoxy-5,6-dihydro-5-hydroxy-6,6-dimethyl-4-(2-oxopiperidin-1-yl)-4H-thieno[2,3-b]pyran; trans-2-acetyl-5,6-dihydro-5-acetoxy-6,6-dimethyl-4-(2-oxopiperidin-1-yl)-4H-thieno[2,3-b]pyran; trans-2-acetyl-5,6-dihydro-5-hydroxy-6,6-dimethyl-4-(2-oxopiperidin-1-yl)-4H-thieno[2,3-b]pyran.

6. A pharmaceutical composition in unit dosage form comprising as the active ingredient a compound of claim 1 in combination with a pharmaceutically acceptable carrier.

7. A method for treating hypertension in a mammal which comprises administering to said mammal an effective amount of a compound of claim 1.

8. A method for treating coronary vasodilation in a mammal which comprises administering to said mammal an effective amount of a compound of claim 1.

* * * * *